US012105310B2

(12) United States Patent
Grot et al.

(10) Patent No.: US 12,105,310 B2
(45) Date of Patent: Oct. 1, 2024

(54) ILLUMINATION OF OPTICAL ANALYTICAL DEVICES

(71) Applicant: Pacific Biosciences of California, Inc., Menlo Park, CA (US)

(72) Inventors: Annette Grot, Cupertino, CA (US); Shang Wang, San Carlos, CA (US); Hans Callebaut, Mountain View, CA (US); Paul Lundquist, San Francisco, CA (US); Stephen Turner, Eugene, OR (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 18/310,315

(22) Filed: May 1, 2023

(65) Prior Publication Data
US 2023/0417975 A1    Dec. 28, 2023

Related U.S. Application Data

(63) Continuation of application No. 17/493,679, filed on Oct. 4, 2021, now Pat. No. 11,640,022, which is a
(Continued)

(51) Int. Cl.
*F21V 8/00*     (2006.01)
*G01N 21/64*    (2006.01)
(Continued)

(52) U.S. Cl.
CPC ......... *G02B 6/0016* (2013.01); *G01N 21/648* (2013.01); *G01N 21/7703* (2013.01);
(Continued)

(58) Field of Classification Search
CPC ...... G02B 6/024; G02B 6/10; G02B 6/12004; G01N 21/648
See application file for complete search history.

(56) References Cited

U.S. PATENT DOCUMENTS

| 5,082,629 A | 1/1992 | Burgess, Jr. et al. |
| 5,094,517 A | 3/1992 | Franke |

(Continued)

FOREIGN PATENT DOCUMENTS

| EP | 1105529 A1 | 6/2001 |
| EP | 1871902 A1 | 1/2008 |

(Continued)

OTHER PUBLICATIONS

Abbas et al. (2011) "Sensitivity Comparison of Surface Plasmon Resonance and Plasmon-Waveguide Resonance Biosensors", Sens. Actuators B Chem. 156: 169-175.
(Continued)

*Primary Examiner* — Daniel Petkovsek
(74) *Attorney, Agent, or Firm* — VLP Law Group LLP

(57) ABSTRACT

Optical analytical devices and their methods of use are provided. The devices are useful in the analysis of highly multiplexed optical reactions in large numbers at high densities, including biochemical reactions, such as nucleic acid sequencing reactions. The devices include optical waveguides for illumination of the optical reactions. The devices further provide for the efficient coupling of optical excitation energy from the waveguides to the optical reactions. Optical signals emitted from the reactions can thus be measured with high sensitivity and discrimination using features such as spectra, amplitude, and time resolution, or combinations thereof. The devices of the invention are well suited for miniaturization and high throughput.

16 Claims, 17 Drawing Sheets

Related U.S. Application Data continuation of application No. 16/805,801, filed on Mar. 1, 2020, now Pat. No. 11,137,532, which is a continuation of application No. 16/030,421, filed on Jul. 9, 2018, now Pat. No. 10,578,788, which is a continuation of application No. 14/945,186, filed on Nov. 18, 2015, now Pat. No. 10,018,764, which is a continuation of application No. 14/107,730, filed on Dec. 16, 2013, now Pat. No. 9,223,084.

(60) Provisional application No. 61/738,637, filed on Dec. 18, 2012.

(51) Int. Cl.
| | |
|---|---|
| *G01N 21/77* | (2006.01) |
| *G02B 6/024* | (2006.01) |
| *G02B 6/10* | (2006.01) |
| *G02B 6/12* | (2006.01) |
| *G02B 6/122* | (2006.01) |
| *G02F 1/365* | (2006.01) |
| *B82Y 15/00* | (2011.01) |
| *B82Y 20/00* | (2011.01) |
| *G02B 23/24* | (2006.01) |

(52) U.S. Cl.
CPC .............. *G02B 6/024* (2013.01); *G02B 6/10* (2013.01); *G02B 6/12004* (2013.01); *G02B 6/122* (2013.01); *G02F 1/365* (2013.01); *B82Y 15/00* (2013.01); *B82Y 20/00* (2013.01); *G01N 21/6452* (2013.01); *G01N 21/6486* (2013.01); *G02B 23/2461* (2013.01)

(56) References Cited

U.S. PATENT DOCUMENTS

| | | |
|---|---|---|
| 5,135,876 A | 8/1992 | Andrade |
| 5,157,262 A | 10/1992 | Marsoner |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,812,709 A | 9/1998 | Arai et al. |
| 5,821,058 A | 10/1998 | Smith et al. |
| 5,832,165 A | 11/1998 | Reichert et al. |
| 5,835,458 A | 11/1998 | Bischel et al. |
| 5,867,266 A | 2/1999 | Craighead |
| 5,919,712 A | 7/1999 | Herron et al. |
| 6,071,748 A | 6/2000 | Modlin et al. |
| 6,192,168 B1 | 2/2001 | Feldstein et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,285,020 B1 | 9/2001 | Kim et al. |
| 6,325,977 B1 | 12/2001 | Theil |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,603,537 B1 | 8/2003 | Dietz et al. |
| 6,611,634 B2 | 8/2003 | Herron et al. |
| 6,690,002 B2 | 2/2004 | Kuroda et al. |
| 6,699,655 B2 | 3/2004 | Nikiforov |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 7,012,687 B2 | 3/2006 | Blumberg et al. |
| 7,022,515 B2 | 4/2006 | Herron et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,170,050 B2 | 1/2007 | Turner et al. |
| 7,175,811 B2 | 2/2007 | Bach et al. |
| 7,181,122 B1 | 2/2007 | Levene et al. |
| 7,189,361 B2 | 3/2007 | Carson et al. |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| RE39,772 E | 8/2007 | Herron et al. |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,400,380 B2 | 7/2008 | Hahn |
| 7,537,734 B2 | 5/2009 | Reichert et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 7,935,310 B2 | 5/2011 | Korlach |
| 8,053,742 B2 | 11/2011 | Lundquist et al. |
| 8,149,657 B2 | 4/2012 | Huang et al. |
| 8,207,509 B2 | 6/2012 | Lundquist et al. |
| 8,247,216 B2 | 8/2012 | Zaccarin et al. |
| 8,274,040 B2 | 9/2012 | Zhong et al. |
| 8,465,699 B2 | 6/2013 | Fehr et al. |
| 8,467,061 B2 | 6/2013 | McCaffrey et al. |
| 8,471,219 B2 | 6/2013 | Lundquist et al. |
| 8,618,507 B1 | 12/2013 | Lundquist et al. |
| 8,906,320 B1 | 12/2014 | Eltoukhy et al. |
| 9,029,802 B2 | 5/2015 | Lundquist et al. |
| 9,223,084 B2 * | 12/2015 | Grot .................. G02B 6/0016 |
| 10,018,764 B2 * | 7/2018 | Grot ..................... G02F 1/365 |
| 11,640,022 B2 * | 5/2023 | Grot ................ G01N 33/54373 |
| | | 385/11 |
| 2002/0034457 A1 | 3/2002 | Reichert et al. |
| 2002/0110839 A1 | 8/2002 | Bach et al. |
| 2002/0113213 A1 | 8/2002 | Amirkhanian et al. |
| 2002/0146047 A1 | 10/2002 | Bendett et al. |
| 2003/0044781 A1 | 3/2003 | Korlach et al. |
| 2003/0174324 A1 | 4/2003 | Sandstrom |
| 2003/0132406 A1 | 7/2003 | Waldhausl et al. |
| 2003/0138180 A1 | 7/2003 | Kondo |
| 2003/0174992 A1 | 9/2003 | Levene et al. |
| 2004/0040868 A1 | 3/2004 | DeNuzzio et al. |
| 2004/0046128 A1 | 3/2004 | Abel et al. |
| 2004/0197793 A1 | 10/2004 | Hassibi et al. |
| 2004/0249227 A1 | 12/2004 | Klapproth et al. |
| 2005/0014178 A1 | 1/2005 | Holm-Kennedy |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0103850 A1 | 5/2006 | Alphonse et al. |
| 2006/0127931 A1 | 6/2006 | Schmidt et al. |
| 2007/0036511 A1 | 2/2007 | Lundquist et al. |

(56) References Cited

U.S. PATENT DOCUMENTS

| | | |
|---|---|---|
| 2007/0099212 A1 | 5/2007 | Harris |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2007/0258096 A1 | 11/2007 | Cui et al. |
| 2008/0020938 A1 | 1/2008 | Kaplan |
| 2008/0039339 A1 | 2/2008 | Hassibi et al. |
| 2008/0151360 A1 | 6/2008 | Stipe |
| 2008/0161195 A1 | 7/2008 | Turner et al. |
| 2008/0212960 A1 | 9/2008 | Lundquist et al. |
| 2008/0278728 A1 | 11/2008 | Tetz et al. |
| 2009/0146076 A1 | 6/2009 | Chiou et al. |
| 2009/0247414 A1 | 10/2009 | Obradovic et al. |
| 2009/0311774 A1 | 12/2009 | Chiou et al. |
| 2009/0312188 A1 | 12/2009 | Duer et al. |
| 2010/0065726 A1* | 3/2010 | Zhong ............... G01N 21/6428 250/227.24 |
| 2010/0121582 A1 | 5/2010 | Pan et al. |
| 2010/0163521 A1 | 7/2010 | Balamane et al. |
| 2010/0255488 A1 | 10/2010 | Kong et al. |
| 2010/0256918 A1 | 10/2010 | Chen et al. |
| 2011/0117637 A1 | 5/2011 | Gray et al. |
| 2011/0210094 A1 | 9/2011 | Gray et al. |
| 2011/0223590 A1 | 9/2011 | Chiou et al. |
| 2011/0301066 A1 | 12/2011 | Blair |
| 2011/0306039 A1 | 12/2011 | Chiou et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0058469 A1 | 3/2012 | Shen |
| 2012/0085894 A1 | 4/2012 | Zhong et al. |
| 2012/0156100 A1 | 6/2012 | Tsai et al. |

FOREIGN PATENT DOCUMENTS

| | | |
|---|---|---|
| EP | 2362209 A2 | 8/2011 |
| KR | 10-2005-0088782 A | 9/2005 |
| WO | 1991006678 | 5/1991 |
| WO | 2001016375 A2 | 3/2001 |
| WO | 2004100068 A2 | 11/2004 |
| WO | 2006116726 A2 | 11/2006 |
| WO | 2006135782 A2 | 12/2006 |
| WO | 2007002367 A2 | 1/2007 |
| WO | 2007011549 A1 | 1/2007 |
| WO | 2008002765 A2 | 1/2008 |
| WO | 2009056065 A1 | 5/2009 |
| WO | 2009131535 A1 | 10/2009 |
| WO | 2009149125 A2 | 12/2009 |
| WO | 2010051773 A1 | 5/2010 |
| WO | 2010102567 A1 | 9/2010 |
| WO | 2011002010 A1 | 1/2011 |
| WO | 2011076132 A2 | 6/2011 |
| WO | 2011105692 A2 | 9/2011 |
| WO | 2014031157 A1 | 2/2014 |

OTHER PUBLICATIONS

Barrios (2006) "Ultrasensitive Nanomechanical Photonic Sensor Based on Horizontal Slot-Waveguide Resonator", IEEE Photon Technol. Lett. 18:2419.

Barrios et al. (2007) "Slot-waveguide biochemical sensor", Optics Letters 32:3080.

Barrios et al. (2008) "Label-free optical biosensing with slot-waveguides", Optics Letters 33:708.

Bernini et al. (2005) "Polymer-on-glass waveguide structure for efficient fluorescence-based optical sensors", Proc. SPIE 5728:101-111.

Boiarski et al. (1992) "Integrated-optic sensor with macro-flow cell", Proc. SPIE 1793:199-211.

Budach et al. (1999) "Planar Waveguides as High-Performance Sensing Platforms for Fluorescence-Based Multiplexed Oligonucleotide Hybridization Assays", Anal. Chem. 71(16):3347-3355.

Chen Chang et al "Focusing plasmons in nanoslits for surface enhanced Raman scattering", Small, Wiley-VCH Verlag Gmbh Co. KGAA, DE, vol. 5, No. 24, Dec. 18, 2009 (Dec. 18, 2009), pp. 2876-2882.

Chen et al. (2012) "Internal Q-switching and self-optical parametric oscillation in a two-dimensional periodically poled Nd:MgO:LiNbO3 laser", Optics Letters 37:2814.

Cottier et al. (2002) "Thickness-modulated waveguides for integrated optical sensing", Proc. SPIE 4616:53-63.

Deopura, M. et al. (2001) "Dielectric omnidirectional visible reflector", Optics Lett 26(15):1197-1199.

Duveneck et al. (2002) "Planar waveguides for ultra-high sensitivity of the analysis of nucleic acids", Anal Chem Acta 469:49-61.

Eid et al. (2009) "Real-Time DNA Sequencing from Single Polymerase Molecules", Science 323:133.

Extended European Search Report dated Jul. 3, 2019 for related EP19165583.6.

Extended European Search Report dated Aug. 4, 2016 for related EP13863794.7.

Feldstein et al. (1999) "Array Biosensor: Optical and Fluidics Systems", J. Biomed Microdev. 1:139-153.

Feng et al. (2006) "Optical Field Concentration in Low-Index Waveguides", IEEE J. Quantum Electron. 42:885.

Feng et al. (2007) "Low-loss compact-size slotted waveguide polarization rotator and transformer", Optics Letters 32:2131.

Fink, Y. et al. (1998) "A Dielectric Omnidirectional Reflector", Science 282:1679-1682.

Herron et al. (2003) "Orientation and Activity of Immobilized Antibodies", Biopolymers at Interfaces 2nd Ed, Surfactant Science Series vol. 110, Marcel Dekker, NY pp. 115-163.

International Search Report and Written Opinion dated Apr. 16, 2014 for related PCT/US2013/075382.

Laurell et al. (2012) "Laser-written waveguides in KTP for broadband Type II second harmonic generation", Optics Express 20:22308.

Levene, M.J. et al. (2003) "Zero-Mode Waveguides for Single-Molecule Analysis at High Concentrations", Science 299:682-686.

Mortazavi et al. (1994) "Quasi-phase-matched frequency doubling in bulk periodic polymeric structures", Optics Letters 19:1290.

Nava et al. (2010) "Integrated frequency shifter in periodically poled lithium tantalite waveguide", Electronics Letters 46:1686.

Pan et al. (2011) "Tuning visible light generation based on multi-channel quasi-periodically poled LiTaO3", Optics Communications 284:429.

Psaltis et al. (2006) "Developing optofluidic technology through the fusion of microfluidics and optics", Nature 442:381.

Robinson et al. (2008) "On-chip gas detection in silicon optical microcavities", Optics Express 16:4296.

Sahin et al. (2011) "Enhanced transmission of electromagnetic waves through split-ring resonator-shaped apertures", J. Nanophoton. 5:051812.

Salama et al. (2004) "Modeling and simulation of luminescence detection platforms", Biosensors Bioelectronics 19:1377-1386.

Saxena et al. Unpublished U.S. Appl. No. 13/920,037, filed Jun. 17, 2013, "Arrays of Integrated Analytical Devices and Methods for Production".

Song et al. (2012) "Polarization properties of surface plasmon enhanced photoluminescence from a single Ag nanowire", Optics Express 20:22290.

Sun et al. (2007) "Horizontal single and multiple slot waveguides: optical transmission at ? = 1550 nm", Optics Express 15:17967.

Wang L et al "Spectral resonance of nanoscale bowtie apertures in visible wavelength", Applied Physics A; Materials Science Processing, Springer, Berlin, DE, vol. 89, No. 2, Jun. 21, 2007 (Jun. 21, 2007), pp. 293-297.

Weissman et al. (1999) "Mach-Zehnder type, evanescent-wave bio-sensor, in ion-exchanged glass, using periodically segmented waveguide", Proc. SPIE 3596:210-216.

William A. Challener et al "Optical Transducers for Near Field Recording", Japanese Journal of Applied Physics, vol. 45, No. 8B, Aug. 1, 2006 (Aug. 1, 2006), pp. 6632-6642.

Wu et al. (2006) "DNA and protein microarray printing on silicon nitride waveguide surfaces", Biosensors and Bioelectronics 21:1252-1263.

(56) References Cited

OTHER PUBLICATIONS

Yao et al. (2012) "Quasi-Phase-Matching Technology", Nonlinear Optics and Solid-State Lasers, Springer-Verlag Berlin Heidelberg, Chapter 5.
Yariv, A. et al. (1977) "Periodic Structures for Integrated Optics", IEEE J Quantum Elec QE-13(4):233-253.
Extended European Search Report dated Sep. 17, 2020 for related EP20175919.8.

* cited by examiner

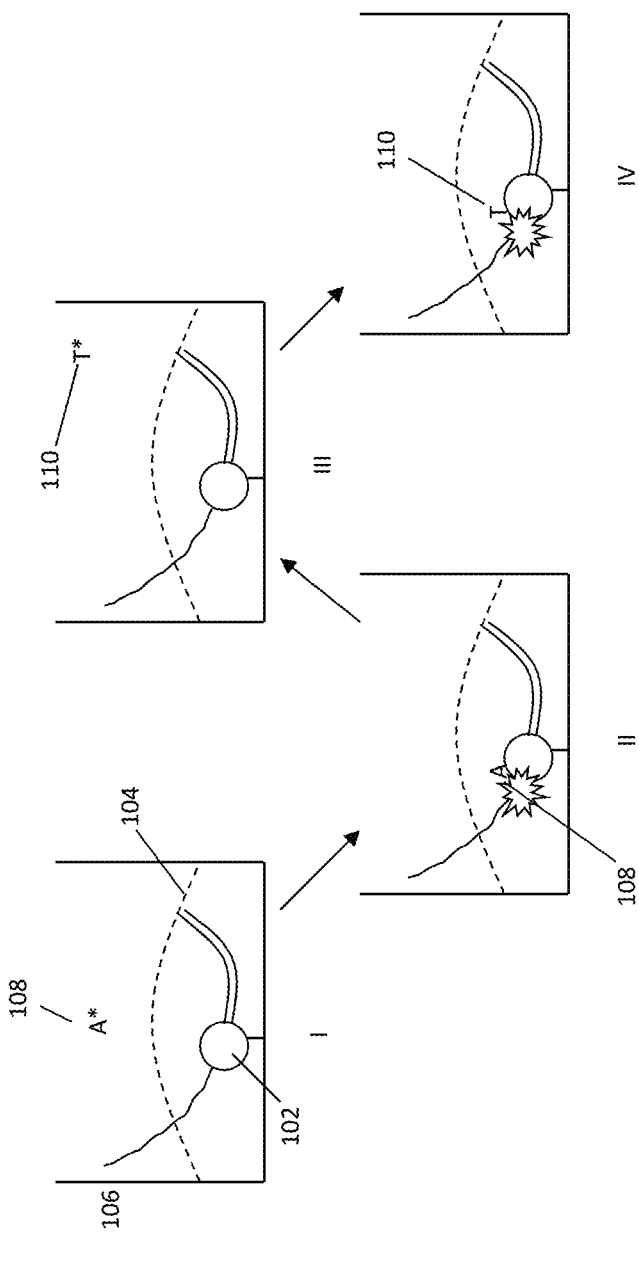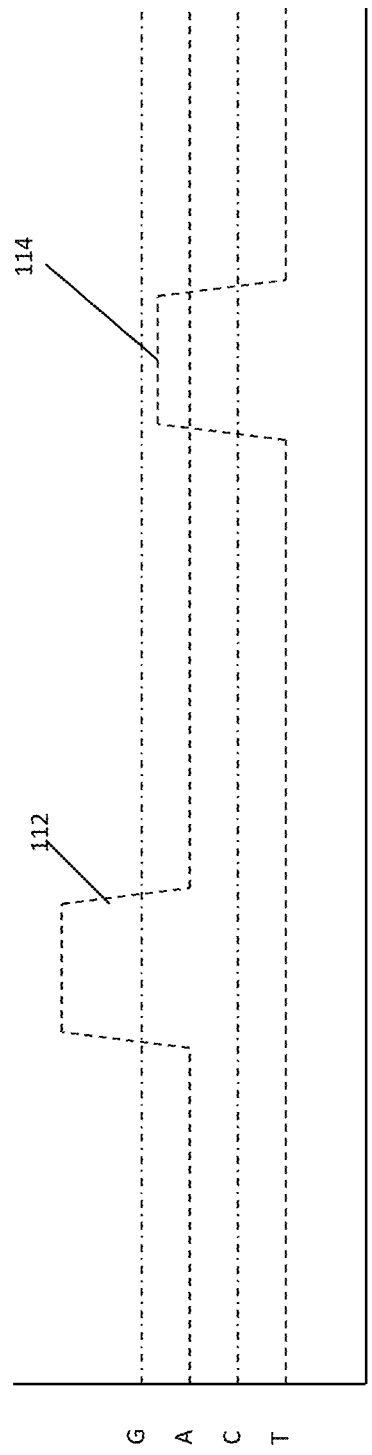
FIG. 1A
FIG. 1B

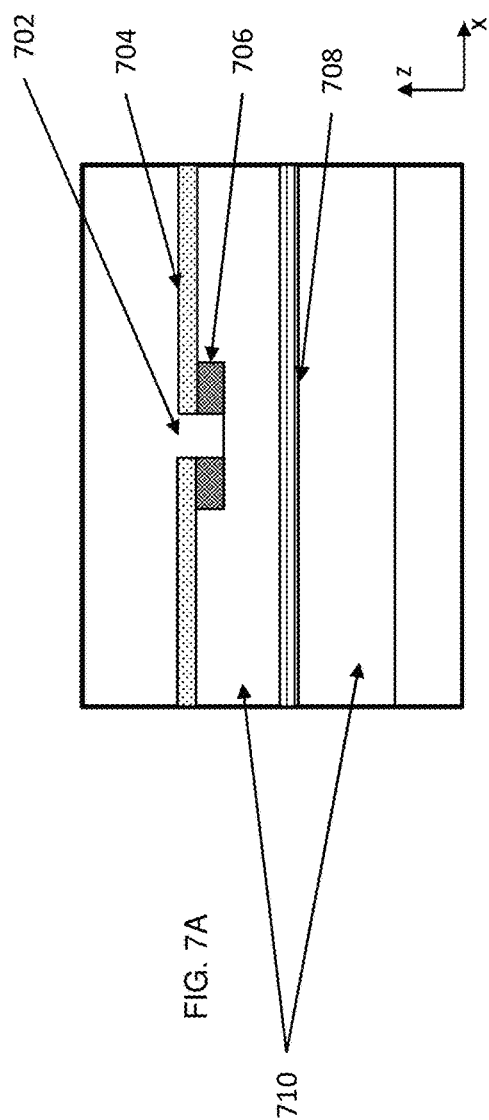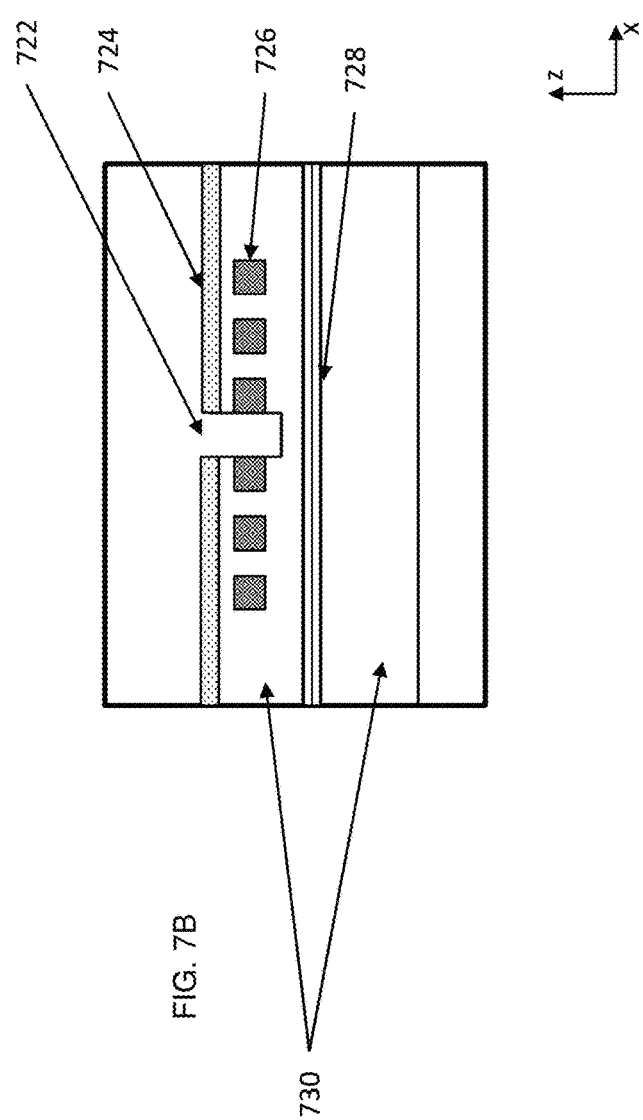

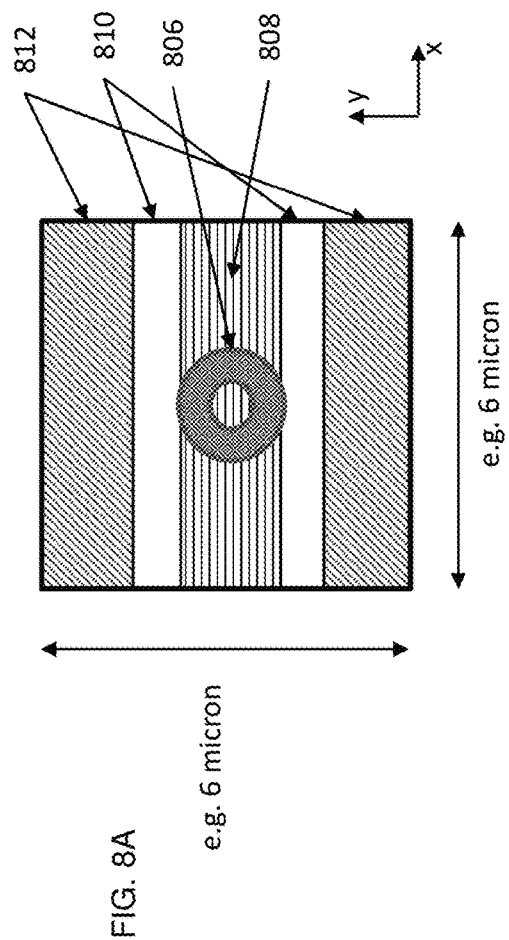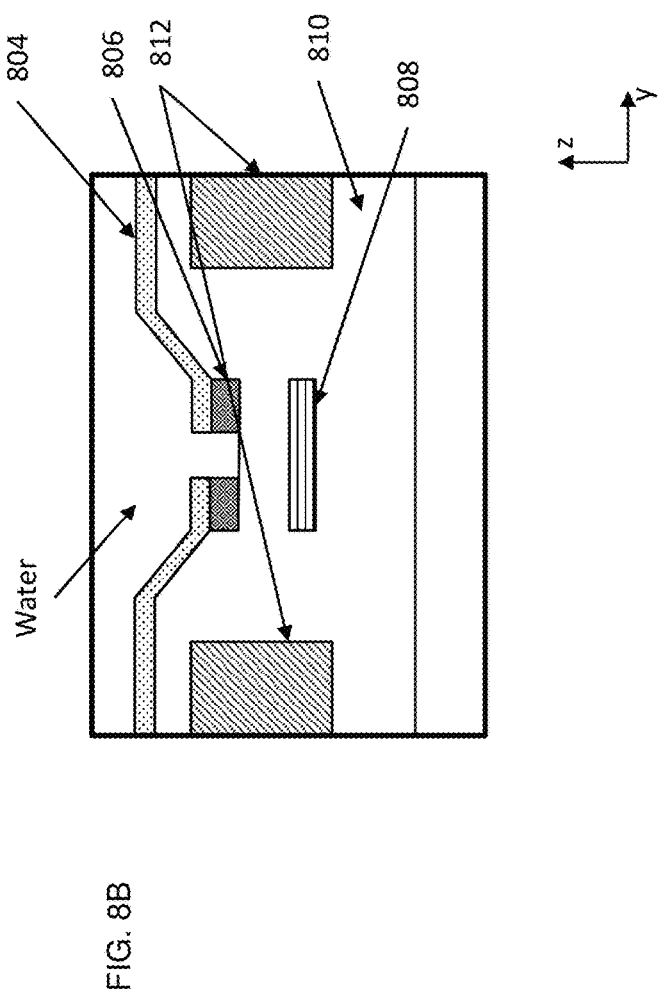

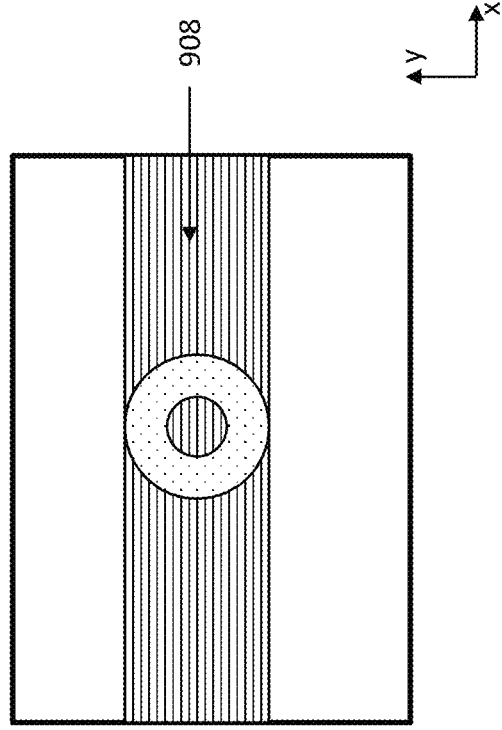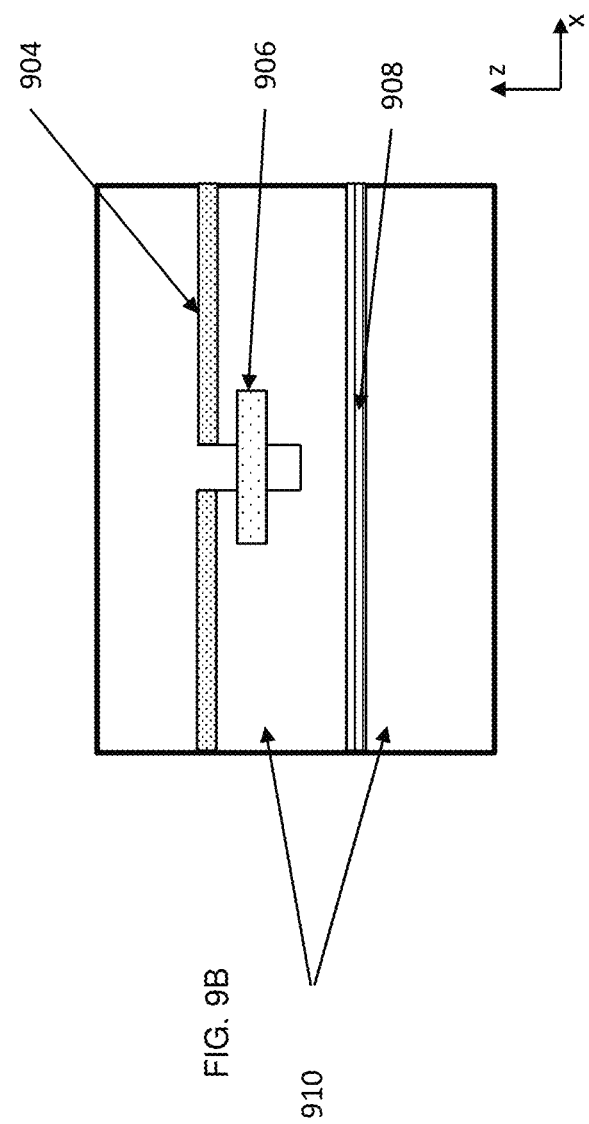
FIG. 9A
FIG. 9B

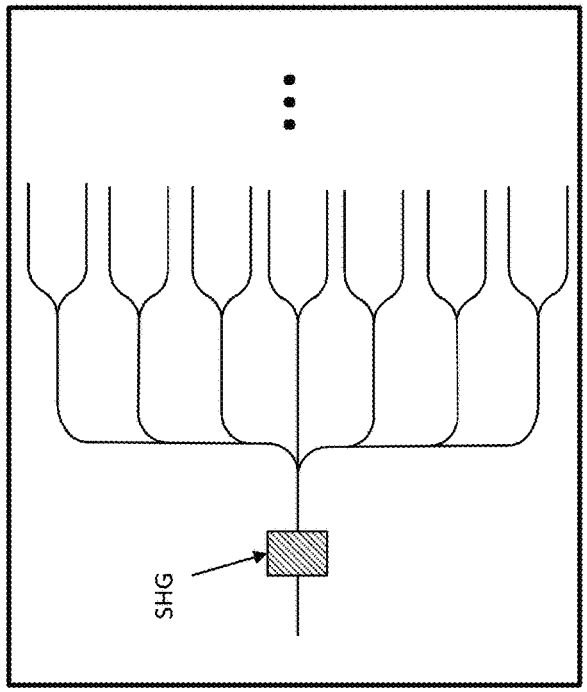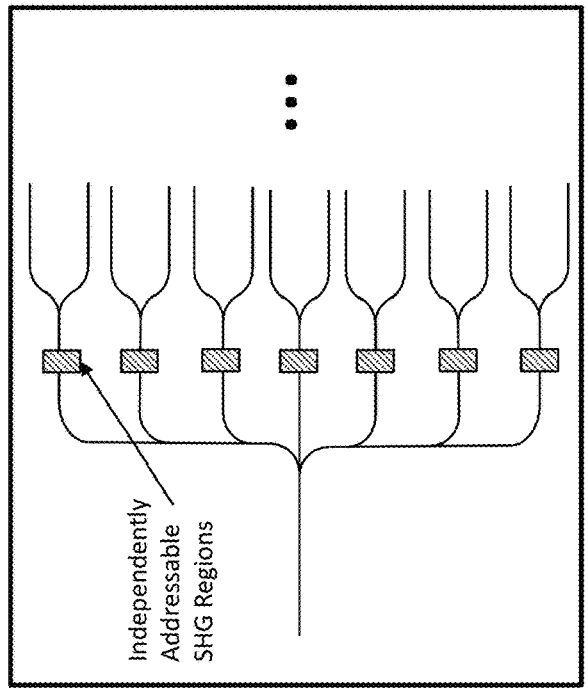

ILLUMINATION OF OPTICAL ANALYTICAL DEVICES

CROSS-REFERENCE TO RELATED APPLICATIONS

This application is a continuation of U.S. patent application Ser. No. 17/493,679, filed on Oct. 4, 2021, now U.S. Pat. No. 11,640,022, which is a continuation of U.S. patent application Ser. No. 16/805,801, filed on Mar. 1, 2020, now U.S. Pat. No. 11,137,532, which is a continuation of U.S. patent application Ser. No. 16/030,421, filed on Jul. 9, 2018, now U.S. Pat. No. 10,578,788, which is a continuation of U.S. patent application Ser. No. 14/945,186, filed on Nov. 18, 2015, now U.S. Pat. No. 10,018,764, which is a continuation of U.S. patent application Ser. No. 14/107,730, filed on Dec. 16, 2013, now U.S. Pat. No. 9,223,084, which claims the benefit under 35 U.S.C. § 119(e) of U.S. Provisional Application No. 61/738,637, filed on Dec. 18, 2012, the disclosures of which are incorporated herein by reference in their entireties.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

In optical analyses, increasing multiplex often poses increased difficulties, as it may require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., in inter reaction cross-talk, decreased signal to noise ratios resulting from either or both of lower signal and higher noise, and the like. It would therefore be desirable to provide analytical systems that have substantially increased multiplex for their desired analysis, and particularly for use in highly sensitive reaction analyses, and in many cases, to do so while minimizing negative impacts of such increased multiplex.

Conventional optical systems employ complex optical trains that direct, focus, filter, split, separate, and detect light to and/or from the sample materials. Such systems typically employ an assortment of different optical elements to direct, modify, and otherwise manipulate light directed to and/or received from a reaction site. Such systems are typically complex and costly and tend to have significant space requirements. For example, typical systems employ mirrors and prisms in directing light from its source to a desired destination. Additionally, such systems may include light-splitting optics such as beam-splitting prisms to generate two or more beams from a single original beam.

There is a continuing need to increase the performance of analytical systems and reduce the cost associated with manufacturing and using the system. In particular, there is a continuing need to increase the throughput of analytical systems. There is a continuing need to reduce the size and complexity of analytical system. There is a continuing need for analytical systems that have flexible configurations and are easily scalable.

SUMMARY OF THE INVENTION

The instant invention addresses these and other problems by providing in one aspect an analytical device comprising an optical waveguide for illumination of nanometer-scale apertures. The waveguide comprises an optical core and a cladding. The device further comprises, in some embodiments, a metallic layer disposed on a surface of the cladding, a plurality of nanometer-scale apertures disposed in the metallic layer in sufficient proximity to the optical waveguide to be illuminated by an evanescent field emanating from the waveguide when optical energy is passed through the optical core, and a plurality of local field enhancement elements associated with the plurality of apertures.

In some embodiments, the local field enhancement elements comprise a high dielectric material or metal in the vicinity of the apertures.

In some embodiments, the high dielectric material or metal of the instant analytical device is arranged in a geometric pattern around the apertures.

In some embodiments, the geometric pattern is selected from the group consisting of a circle, a series of concentric circles, a C aperture, a triangle pair, and a diamond. In specific embodiments, the high dielectric material or metal is $Al_2O_3$, copper, silver, gold, or aluminum. In more specific embodiments, the high dielectric material or metal is $Al_2O_3$. In other more specific embodiments, the high dielectric material or metal is copper.

In some embodiments, the apertures of the device are recessed into the cladding. In some embodiments, the thickness of the cladding between the optical core and the metallic layer decreases in the vicinity of the apertures. In specific embodiments, the thickness of the cladding is from 150 to 300 nm. In more specific embodiments, the thickness of the cladding is about 200 nm.

In certain embodiments, the local field enhancement elements comprise the shape of the nanometer-scale apertures. In specific embodiments, the shape of the nanometer-scale apertures is selected from the group consisting of a C aperture, a triangle pair, and a diamond.

In another aspect, the invention provides an analytical device comprising an optical waveguide comprising an optical core and a cladding, a metallic layer disposed on the surface of the cladding; and a plurality of nanometer-scale apertures disposed in the metallic layer in sufficient proximity to the optical waveguide to be illuminated by an evanescent field emanating from the waveguide when optical energy is passed through the optical core, wherein the optical core has a thickness, a width, and a cross-sectional area, and wherein the cross-sectional area is decreased at locations where the evanescent field illuminates the apertures.

In some embodiments, the cross-sectional area of the optical core is decreased by adiabatic tapers.

In some embodiments, the thickness of the optical core is maintained, and the cross-sectional area is decreased by decreasing the width of the optical core. In preferred embodiments, the optical energy is transverse electric polarized light.

In some embodiments, the width of the optical core is maintained, and the cross-sectional area is decreased by decreasing the thickness of the optical core. In preferred embodiments, the optical energy is transverse magnetic polarized light.

In some embodiments, the analytical device further comprises a plurality of local field enhancement elements associated with the plurality of apertures, as described above.

In another aspect, the invention provides an analytical device comprising an optical waveguide comprising a plurality of optical cores and a cladding, a plurality of nanometer-scale apertures disposed on a surface of the device in sufficient proximity to the optical waveguide to be illuminated by an evanescent field emanating from the waveguide when optical energy is passed through the plurality of optical cores, and a plurality of detectors optically coupled to the plurality of nanometer-scale apertures, wherein the optical cores are not in direct alignment between the nanometer-scale apertures and their optically coupled detectors.

In preferred embodiments, the plurality of nanometer-scale apertures are illuminated by an evanescent field emanating from at least two optical cores. In other preferred embodiments, the analytical device further comprises an opaque layer disposed between the optical waveguide and the plurality of optical detectors, wherein the opaque layer comprises a plurality of openings in direct alignment with the nanometer-scale apertures and their optically coupled detectors. In still other preferred embodiments, the device further comprises a plurality of local field enhancement elements associated with the plurality of apertures, as described above.

In yet another aspect, the invention provides an analytical device comprising an optical waveguide comprising an optical core and a cladding, and a plurality of nanometer-scale apertures disposed on a surface of the device in sufficient proximity to the optical waveguide to be illuminated by an evanescent field emanating from the waveguide when optical energy of a defined wavelength is passed through the optical core, wherein the wavelength of the optical energy is modulated as it passes through the optical core.

In some embodiments of the analytical device, the optical waveguide comprises a non-linear optical material. In preferred embodiments, the non-linear optical material is placed periodically within the optical core. In other preferred embodiments, the non-linear optical material is placed within the cladding.

In particularly preferred embodiments, the wavelength conversion is effected through phase matching. In other particularly preferred embodiments, the wavelength conversion is effected through electro-optical effects.

In some embodiments, the optical energy is modulated by second harmonic generation. In other embodiments, the optical energy is modulated by third harmonic generation.

In some embodiments, the optical energy is modulated by optical parametric amplification. In some embodiments, the device further comprises a plurality of local field enhancement elements associated with the plurality of apertures, as described above.

In some embodiments, the analytical device further comprises a plurality of analytes disposed in analyte regions within the plurality of nanometer-scale apertures. In specific embodiments, the plurality of analytes comprise a plurality of biological samples. In preferred embodiments, the plurality of biological samples comprise a plurality of nucleic acids. In more preferred embodiments, the analytical device comprises at least 1,000, at least 10,000, at least 100,000, at least 1,000,000, or at least 10,000,000 nanometer-scale apertures.

BRIEF DESCRIPTION OF THE DRAWINGS

FIGS. 1A and 1B schematically illustrate an exemplary nucleic acid sequencing process that can be carried out using aspects of the invention.

FIG. 7A illustrates an analytical device containing a waveguide core, cladding, metallic/opaque layer, and a material of high dielectric or metal in the vicinity of the nanometer-scale aperture, as viewed in the x-z plane. FIG. 7B illustrates an alternative device structure, having a geometric pattern of high dielectric material or metal surrounding the aperture.

FIGS. 8A and 8B illustrate an analytical device where the thickness of the cladding is decreased in the regions of waveguide adjacent to the aperture, and the device additionally contains a stray light termination material. FIG. 8A shows a top view in the x-y plane with the opaque, metallic layer omitted from the view. FIG. 8B shows a cross-sectional view in the y-z plane.

FIGS. 9A-9C provide a schematic of the design used in simulations of coupling efficiencies. FIG. 9A shows a top view of the simulated device in the x-y plane with the opaque, metallic layer omitted from the view. FIG. 9B shows a side view of the simulated device in the x-z plane. FIG. 9C shows a cross-sectional view of the simulated device in the y-z plane.

FIG. 11A: cross-sectional view; FIG. 11B: top-down view.

FIGS. 14A and 14B schematically illustrate a waveguide containing a wavelength conversion element just after the coupler (FIG. 14A) and another exemplary waveguide with independently addressable SHG elements (FIG. 14B).

DETAILED DESCRIPTION OF THE INVENTION

Integrated Optical Detection Devices

Figure 2:
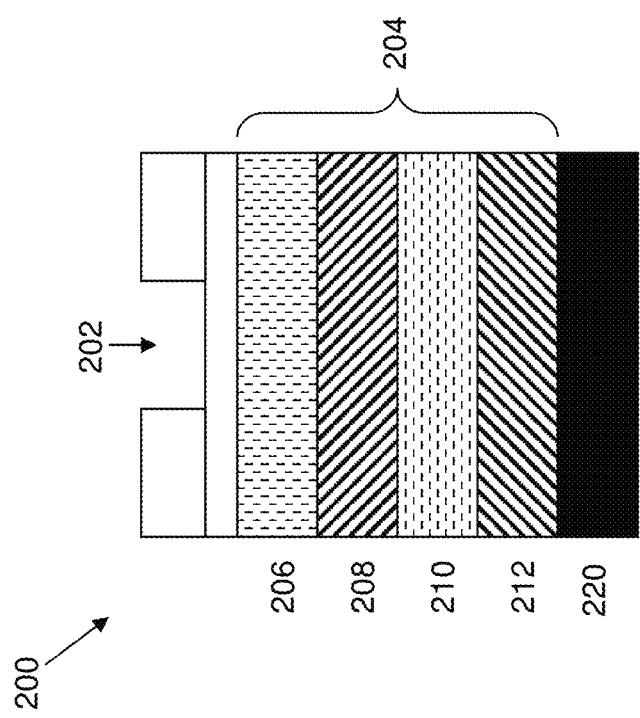
FIG. 2 provides a schematic block diagram of an integrated analytical device.

Multiplexed optical analytical systems are used in a wide variety of different applications. Such applications can include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the devices and systems described herein are of broader application.

In the context of single molecule nucleic acid sequencing analyses, a single immobilized nucleic acid synthesis complex, comprising a polymerase enzyme, a template nucleic acid, whose sequence is being elucidated, and a primer sequence that is complementary to a portion of the template sequence, is observed in order to identify individual nucleotides as they are incorporated into the extended primer sequence. Incorporation is typically monitored by observing an optically detectable label on the nucleotide, prior to, during, or following its incorporation. In some cases, such single molecule analyses employ a "one base at a time approach", whereby a single type of labeled nucleotide is introduced to and contacted with the complex at a time. Upon reaction, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type of nucleotide is contacted with the complex at any given time, any incorporation event is, by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but the nucleotides are distinguishable by the presence on each type of nucleotide a different optical label. Accordingly, such methods can use a single step to identify a given base in the sequence. In particular, all four nucleotides, each bearing a distinguishable label, are added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another example, single molecule primer extension reactions are monitored in real time, to identify the continued incorporation of nucleotides in the extension product to elucidate the underlying template sequence. In such single molecule real time (or SMRT™) sequencing, the process of incorporation of nucleotides in a polymerase-mediated template-dependent primer extension reaction is monitored as it occurs. In preferred aspects, the template/polymerase primer complex is provided, typically immobilized, within an optically-confined region, such as a zero mode waveguide (ZMW), or proximal to the surface of a transparent substrate, optical waveguide, or the like (see e.g., U.S. Pat. Nos. 6,917,726, 7,170,050, and 7,935,310, the full disclosures of which are hereby incorporated by reference herein in their entirety for all purposes). The optically-confined region is illuminated with an appropriate excitation radiation for the fluorescently-labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated.

A schematic illustration of this sequencing process is shown in FIGS. 1A and 1B. As shown in FIG. 1A, an immobilized complex 102 of a polymerase enzyme, a template nucleic acid and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation. The incorporation reaction thus produces a signal associated with that retention, e.g., signal pulse 112 as shown by the A trace in FIG. 1B. Once incorporated, the label that was attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

The above sequencing reaction may be incorporated into a device, typically an integrated analytical device, that provides for the simultaneous observation of multiple sequencing reactions, ideally in real time. While the components of each device, and the configuration of the devices in the system, may vary, each integrated analytical device typically comprises, at least in part, the general structure shown as a block diagram in FIG. 2. As shown, an integrated analytical device 200 typically includes a reaction cell 202, in which the reactants are disposed and from which the optical signals emanate. The analysis system further includes a detector element 220, which is disposed in optical communication with the reaction cell 202. Optical communication between the reaction cell 202 and the detector element 220 may be provided by an optical train 204 comprised of one or more optical elements generally designated 206, 208, 210 and 212 for efficiently directing the signal from the reaction cell 202 to the detector 220. These optical elements may generally comprise any number of elements, such as lenses, filters, gratings, mirrors, prisms, refractive material, or the like, or various combinations of these, depending upon the specifics of the application. By integrating these elements into a single device architecture, the efficiency of the optical coupling between the reaction cell and the detector is improved. Examples of integrated analytical systems, including various approaches for illuminating the reaction cell and detecting optical signals emitted from the reaction cell, are described in U.S. Patent Application Publication Nos. 2012/0014837, 2012/0019828, and 2012/0021525, which are each incorporated by reference herein in their entireties for all purposes.

Conventional analytical systems typically measure multiple spectrally distinct signals or signal events and must therefore utilize complex optical systems to separate and distinctly detect those different signal events. The optical path of an integrated device may be simplified, however, by a reduction in the amount or number of spectrally distinguishable signals that are detected. Such a reduction is ideally effected, however, without reducing the number of distinct reaction events that can be detected. For example, in an analytical system that distinguishes four different reactions based upon four different detectable signal events, where a typical system would assign a different signal spectrum to each different reaction, and thereby detect and distinguish each signal event, in an alternative approach, four different signal events would be represented at fewer than four different signal spectra, and would, instead, rely, at least in part, on other non-spectral distinctions between the signal events.

For example, a sequencing operation that would conventionally employ four spectrally distinguishable signals, e.g., a "four-color" sequencing system, in order to identify and characterize the incorporation of each of the four different nucleotides, would, in the context of an alternative configuration, employ a one-color or two-color analysis, e.g., relying upon a signals having only one or two distinct or distinguished spectral signals. However, in such an alternative configuration, this reduction in reliance on signal spectral complexity does not come at the expense of the ability to distinguish signals from multiple, i.e., a larger number of different signal producing reaction events. In particular, instead of relying solely on signal spectrum to distinguish reaction events, such an alternative configuration may rely upon one or more signal characteristics other than emission spectrum, including, for example, signal intensity, excitation spectrum, or both to distinguish signal events from each other.

In one particular alternative configuration, the optical paths in an integrated analytical device may thus be simplified by utilizing signal intensity as a distinguishing feature between two or more signal events. In its simplest iteration, and with reference to an exemplary sequencing process, two different types of nucleotides would bear fluorescent labels that each emit fluorescence under the same excitation illumination, i.e., having the same or substantially overlapping spectral band, and thus would provide benefits of being excited using a single excitation source and beam. The resulting signals from each fluorescent label would have distinct signal intensities or amplitudes under that same illumination, and would be distinguishable by their respective signal amplitudes. These two signals could have partially or entirely overlapping emission spectra, but separation of the signals based upon any difference in emission spectrum would be unnecessary.

Accordingly, for analytical systems using two or more signal events that differ in signal amplitude, the integrated analytical devices of such systems can readily benefit through the removal of some or all of those components that would normally be used to separate spectrally distinct signals, such as multiple excitation sources and their associated optical trains, as well as the color separation optics, e.g., filters and dichroics, for the signal events, which in many cases, requires at least partially separate optical trains and detectors for each spectrally distinct signal. As a result, the optical paths for these integrated analytical devices are greatly simplified, allowing placement of detector elements in closer proximity to reaction regions, and improving overall performance of the detection process for these devices.

Figure 3A:
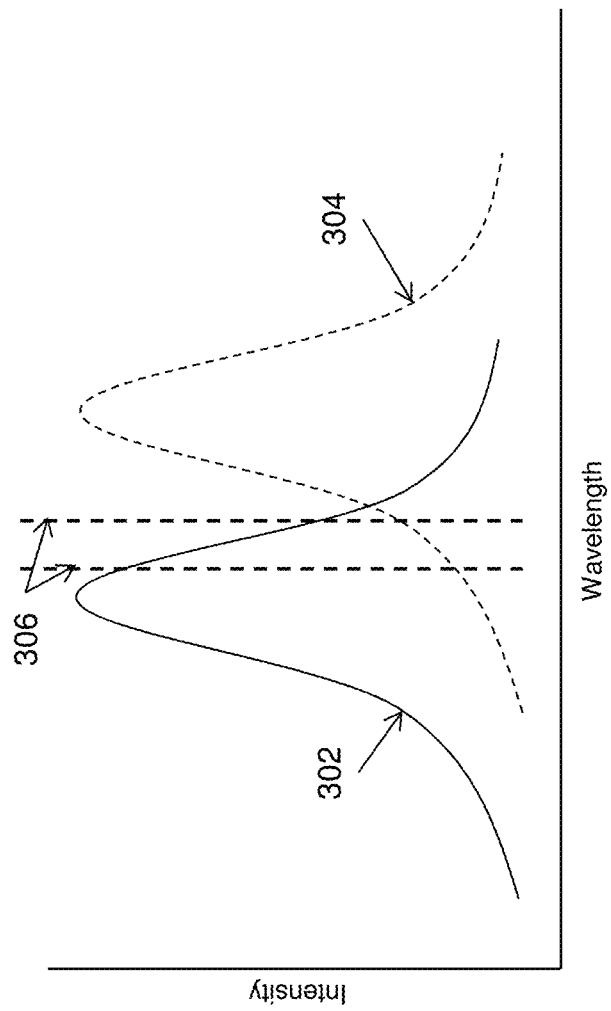
FIG. 3A provides a schematic of excitation spectra for two signal events and an indicated narrow band excitation illumination, while FIG. 3B schematically illustrates the resulting detected signal based upon the narrow band illumination of the two signal events.
Figure 3B:
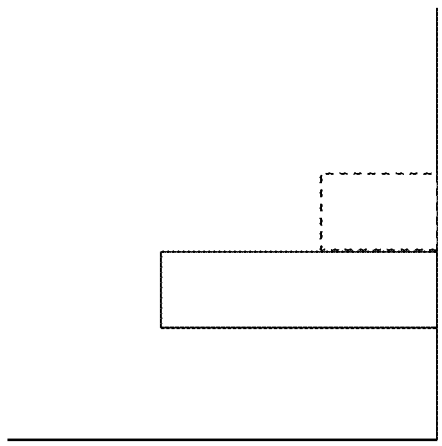

Provision of signal-producing reactants that will produce different signal amplitudes under a particular excitation illumination profile may be accomplished in a number of ways. For example, different fluorescent labels may be used that present excitation spectral profiles that overlap but include different maxima. As such, excitation at a narrow wavelength will typically give rise to differing signal intensities for each fluorescent group. This is illustrated in FIG. 3A, which shows the excitation spectra of two different fluorescent label groups (solid and dashed lines 302 and 304, respectively). When subjected to excitation illumination at the wavelength range shown by vertical lines 306, each fluorescent label will emit a signal at the corresponding amplitude. The resulting signal intensities at a given excitation wavelength are then shown in the bar chart of FIG. 3B, shown as the solid lined and dashed lined bars, respectively. The difference in intensity of these two signal-producing labels at the given excitation wavelength can then be readily used to distinguish the two signal events. As will be appreciated, such spectrally indistinct signals would not be easily distinguishable when occurring simultaneously, as they would result in an additive overlapping signal, unless, as discussed below, such spectrally indistinct signals result from spectrally distinct excitation wavelengths. As will be appreciated, this same approach may be used with more than two label groups where the resulting emission at a given excitation spectrum have distinguishable intensities or amplitudes.

Similarly, two different fluorescent labeling groups may have the same or substantially similar excitation spectra, but provide different and distinguishable signal emission intensities due to the quantum yield or extinction coefficient of those labeling groups.

Further, although described in terms of two distinct fluorescent dyes, it will be appreciated that each different labeling group may each include multiple labeling molecules. For example, each reactant may include an energy transfer dye pair that yields emissions of differing intensities upon excitation with a single illumination source. For example, a labeling group may include a donor fluorophore that is excited at a given excitation wavelength, and an acceptor fluorophore that is excited at the emission wavelength of the donor, resulting in energy transfer to the acceptor. By using different acceptors, whose excitation spectra overlap the emission spectrum of the donor to differing degrees, such an approach can produce overall labeling groups that emit at different signal amplitudes for a given excitation wavelength and level. Likewise, adjusting the energy transfer efficiency between the donor and acceptor will likewise result in differing signal intensities at a given excitation illumination. Examples of these approaches are described in U.S. Patent Application Publication No. 2010/0255488, the full disclosure of which is incorporated by reference herein in its entirety for all purposes.

Alternatively, different signal amplitudes may be provided by different multiples of signal producing label groups on a given reactant, e.g., putting a single label molecule on one reactant while putting 2, 3, 4 or more individual label molecules on a different reactant. The resulting emitted signal will be reflective of the number of labels present on a reactant and thus will be indicative of the identity of that reactant. Methods and compositions for coupling multiple labeling groups on reactants, such as nucleotide analogs, are described in, for example, U.S. patent application Ser. No. 13/218,312, filed Aug. 25, 2011, and incorporated by reference herein in its entirety for all purposes.

As described above, integrated analytical devices making use of such approaches see a reduction in complexity by elimination of spectral discrimination requirements, e.g., using signal amplitude or other non-spectral characteristics as a basis for signal discrimination. Integrated analytical devices that combine such non-spectral discrimination approaches with the more common spectral discrimination approaches may also provide advantages over more complex spectral discrimination systems. By shifting from a "four-color" discrimination system to a system that distinguishes signals based upon signal intensity and color, one can still reduce the complexity of the overall optical system relative to a conventional four-color separation scheme. For example, in an analytical operation that detects four discrete reaction events, e.g., in a nucleic acid sequencing analysis, two signal events may be provided within a given emission/detection spectrum, i.e., emitting signals within the same spectral window, and the other two events within a distinct emission/detection spectrum. Within each spectral window, the pair of signal events produce distinguishable signal intensities relative to each other.

Figure 4:
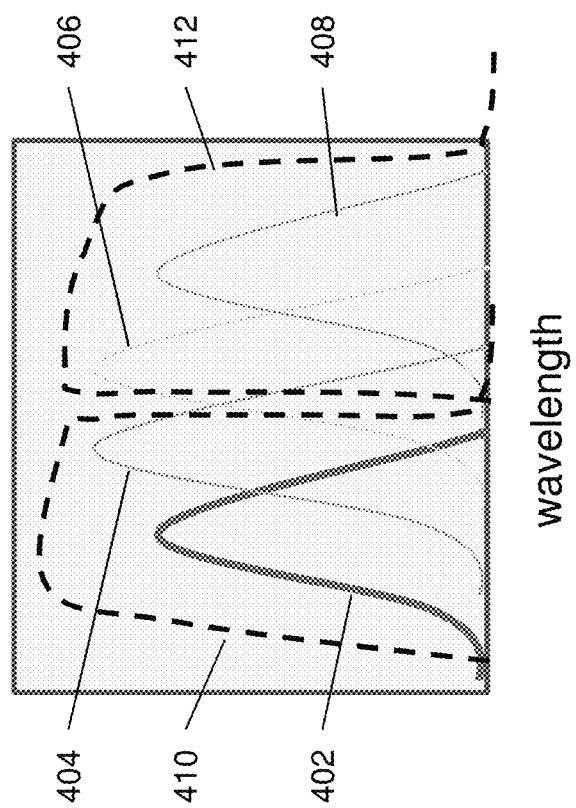
FIG. 4 schematically illustrates the signal profiles for each of four fluorescent labeling groups, overlain with each of two different filter profiles.

For ease of discussion, this concept is described in terms of two groups of fluorescent signal events, where members of each group differ by fluorescent intensity, and the groups differ by virtue of their emission spectrum. As will be appreciated, the use of simplified optics systems, e.g., using two detection channels for two distinct emission spectra, does not require that the emission profiles of the two groups of signals do not overlap or that the emission spectra of members of each group perfectly overlap. Instead, in many preferred aspects, more complex signal profiles may be used where each different signal event possesses a unique emission spectrum, but in a way that each signal will present a signal profile within the two detection channels that is unique, based upon the signal intensity in each channel FIG. 4 schematically illustrates the signal profiles for each of four fluorescent labeling groups, overlain with each of two different filter profiles. As shown, four label groups yield emission spectra 402, 404, 406 and 408, respectively. While the signals from these four groups partially overlap each other, they each have different maxima When subjected to a two channel filter scheme, as shown by pass filter lines 410 and 412, the signal from each label will produce a unique signal profile between the two detection channels. In particular, signals are routed through an optical train that includes two paths that are filtered according to the spectral profile shown. For each signal, different levels of emitted light will pass through each path and be detected upon an associated detector. The amount of signal that passes through each filter path is dictated by the spectral characteristics of the signal.

In the case of the above described mixed-mode schemes, detection systems may be provided that include at least two distinct detection channels, where each detection channel passes light within a spectrum that is different from each other channel. Such systems also include a reaction mixture within optical communication of the detection channels, where the reaction mixture produces at least three different optical signals that each produces a unique signal pattern within the two detection channels, as compared to the other optical signals.

In each case, each signal-producing reactant is selected to provide a signal that is entirely distinct from each other signal in at least one of signal intensity and signal channel As noted above, signal intensity in a given channel is dictated, in part, by the nature of the optical signal, e.g., its emission spectrum, as well as the filters through which that signal is passed, e.g., the portion of that spectrum that is allowed to reach the detector in a given channel However, signal intensity can also be modulated by random variables, such as orientation of a label group when it is emitting signal, or other variables of the particular reaction. Accordingly, for a signal's intensity to be assured of being entirely different from the intensity of another signal within a given channel, in preferred aspects, this variation is accounted for.

Figure 5:
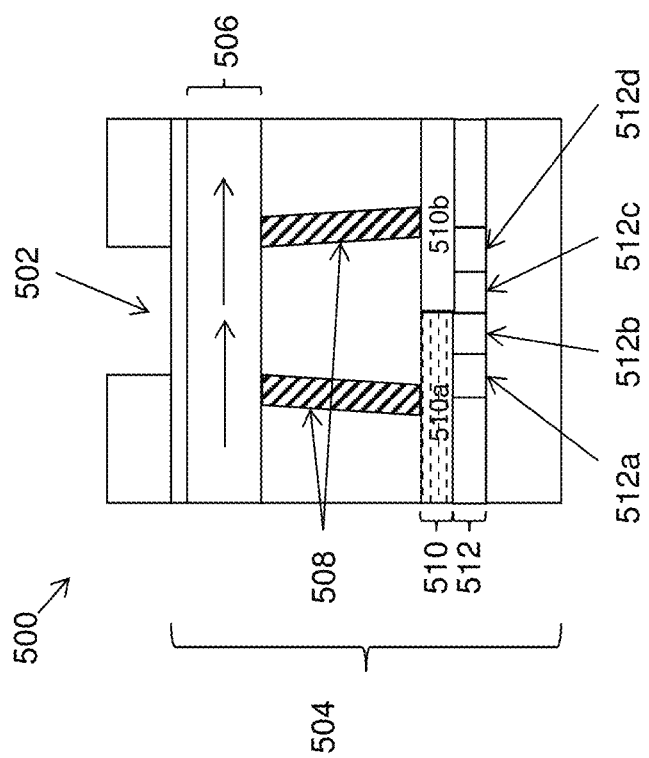
FIG. 5 schematically illustrates an integrated analytical device for detecting signals from a 4-color sequencing reaction.

With a reduced number of spectrally distinct signal events, the complexity of the optical paths for the integrated devices is also reduced. FIG. 5 illustrates a not-to-scale example device architecture for performing optical analyses, e.g., nucleic acid sequencing processes, that rely in part on non-spectral discrimination of differing signals, and optionally, in part on spectral distinction. As shown, an integrated analytical device 500 includes a reaction region 502 that is defined upon a first substrate layer 504. As shown, the reaction region comprises a well disposed in the substrate surface. Such wells may constitute depressions in a substrate surface or apertures disposed through additional substrate layers to an underlying transparent substrate, e.g., as used in zero mode waveguide arrays (See, e.g., U.S. Pat. Nos. 7,181,122 and 7,907,800).

In the device of FIG. 5, excitation illumination is delivered to the reaction region from an excitation light source (not shown) that may be separate from or also integrated into the substrate. As shown, an optical waveguide (or waveguide layer) 506 may be used to convey excitation light (shown by arrows) to the reaction region/well 502, where the evanescent field emanating from the waveguide 506 illuminates reactants within the reaction region 502. Use of optical waveguides to illuminate reaction regions is described in e.g., U.S. Pat. No. 7,820,983 and U.S. Patent Application Publication No. 2012/0085894, which are each incorporated by reference herein in their entireties for all purposes.

The integrated device 500 optionally includes light channeling components 508 to efficiently direct emitted light from the reaction regions to a detector layer 512 disposed beneath the reaction region. The detector layer typically comprises one, or preferably multiple, detector elements 512a-d, e.g., pixels in an array detector, that are optically coupled to a given reaction region. Although illustrated as a linear arrangement of pixels 512a-d, it will be appreciated that such pixels may be arranged in a grid, n×n square, annular array, or any other convenient orientation.

Emitted signals from the reaction region 502 that impinge on these pixels are then detected and recorded. As noted above, an optional single filter layer 510 is disposed between the detector layer and the reaction region, to permit different spectrally distinct signals to travel to different associated pixels 512a and 512b in the detector layer 512. For example, the portion 510a of filter layer 510 allows signals having a first emission spectrum to reach its associated pixels 512a and 512b, while filter portion 510b of filter layer 510 allows only signals having a distinct second spectrum to reach its associated pixels 512c and 512d.

In the context of a sequencing system exploiting such a configuration, incorporation of two of the four nucleotides would produce signals that would be passed through filter portion 510a to pixels 512a and 512b, and blocked by filter portion 510b. As between these two signals, one signal would have a signal intensity higher than the other such that the pixels 512a and 512b in detector layer 512 would be able to produce signal responses indicative of such differing signal intensities. Likewise, incorporation of the other two nucleotides would produce signals that would be passed through filter portion 510b to its associated pixels 512c and 512d, while filter portion 510a would block those signals from reaching pixels 510a and 510b. Again, the signals associated with these two latter signal events would differ based upon their signal intensities or amplitudes.

The detector layer is then operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Patent Application Publication No. 2012/0019828.

As will be appreciated from the foregoing disclosure and FIG. 5, the integrated analytical devices described herein do not require the more complicated optical paths that are necessary in systems utilizing conventional four-color optics, obviating the need for excessive signal separation optics, dichroics, prisms, or filter layers. In particular, although shown with a single filter layer, as noted, in optional aspects, the filter layer could be eliminated or could be replaced with a filter layer that blocks stray light from the excitation source rather than distinguishing different emission signals from the reaction region. Even including the filter layer 510, results in simplified and/or more efficient optics as compared to conventional four-color systems, which would require either multilayer filters, or narrow band pass filters, which typically require hybrid layers or composite approaches over each subset of pixels, thus blocking signal from reaching three of the four pixel subsets at any given emission wavelength, resulting in detection of far fewer photons from each signal event. The optics configuration shown in FIG. 5, on the other hand, only blocks a smaller portion of the overall signal light from reaching the detector. Alternatively, such conventional systems would require separation and differential direction of all four different signal types, resulting in inclusion of additional optical elements, e.g., prisms or gratings, to achieve spectral separation.

Figure 6:
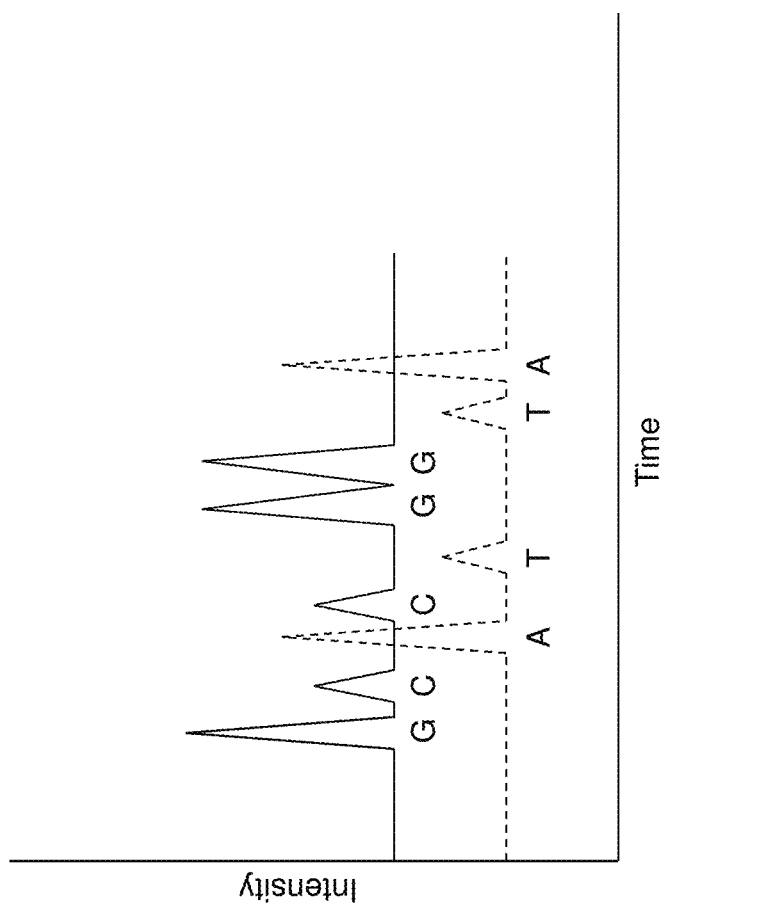
FIG. 6 schematically illustrates signal traces for a two-color, two-amplitude sequence-by-synthesis reaction.

FIG. 6 shows a schematic exemplar signal output for a real time sequencing operation using a two color/two amplitude signal set from an integrated system of the invention where one trace (dashed) denotes signals associated with incorporation of A (high intensity signal) and T (lower intensity signal) bases, while the other signal trace (solid line), denotes the signals of a different emission spectrum, associated with G (high) and C (low) bases. The timing of incorporation and the identity of the base incorporated, as derived from the color channel and intensity of the signal, are then used to interpret the base sequence.

Arrays of Integrated Optical Detection Devices

In order to obtain the volumes of sequence information that may be desired for the widespread application of genetic sequencing, e.g., in research and diagnostics, higher throughput systems are desired. By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments.

As described above, and as shown in FIGS. 1A, the template/DNA polymerase-primer complex of such a sequencing system is provided, typically immobilized, within an optically confined region, such as a zero mode waveguide (ZMW), or proximal to the surface of a transparent substrate, optical waveguide, or the like. Preferably, such reaction cells are arrayed in large numbers upon a substrate in order to achieve the scale necessary for genomic or other large-scale DNA sequencing approaches. Such arrays preferably comprise a complete integrated analytical device, such as, for example, the devices shown in the block diagrams of FIGS. 2 and 5. Examples of integrated systems comprising arrays of optical analytical devices are provided in U.S. Patent Application Publication Nos. 2012/0014837; 2012/0019828; and 2012/0021525.

Arrays of integrated analytical devices, such as arrays of devices comprising ZMWs, can be fabricated at ultra-high density, providing anywhere from 1000 ZMWs per cm$^2$, to 10,000,000 ZMWs per cm$^2$, or more. Thus, at any given time, it may be desirable to analyze the reactions occurring in 100, 1000, 3000, 5000, 10,000, 20,000, 50,000, 100,000, 1 Million, 5 Million, 10 Million, or more ZMWs or other reaction regions within a single analytical system or even on a single substrate.

Using the foregoing systems, simultaneous targeted illumination of thousands or tens of thousands of ZMWs in an array has been described. However, as the desire for multiplex increases, the density of ZMWs on an array, and the ability to provide targeted illumination of such arrays, increases in difficulty, as issues of ZMW cross-talk (signals from neighboring ZMWs contaminating each other as they exit the array), decreased signal:noise ratios arising from higher levels of denser illumination, and the like, increase. The devices and methods of the instant invention address some of these issues.

The position on the detector upon which a given signal is incident is indicative of (1) the originating ZMW in the array, and (2) the emission characteristics of the signal component, which is used, for example, to identify the type of fluorescently labeled nucleotide analog incorporated in an extension reaction. As noted above, the detector may include in some cases multiple sensing elements, each for detecting light having a different color spectrum. For example, in the case of sequencing, the sensor for each reaction cell may have 4 elements, one for each of the four bases. In some cases, the sensor elements provide color discrimination, in other cases, color filters are used to direct the appropriate color of light to the appropriate sensor element. In some cases, the sensor elements detect intensity of signal only, without discriminating color. In some cases, the sensor elements identifies the incorporated nucleotide using a combination of emission characteristics.

Optical Waveguides

As mentioned above, the analytical devices of the instant invention, in some embodiments, comprise an optical waveguide to deliver excitation energy to a sample. For example, as shown in FIG. 5, optical waveguide 506 conveys excitation light to the reaction region/well 502, where the evanescent field emanating from the waveguide 506 illuminates reactants within the reaction region 502. The use of an optical waveguide to deliver excitation illumination is advantageous for numerous reasons. For example, because the illumination light is applied in a spatially focused manner, e.g., confined in at least one lateral and one orthogonal dimension, using efficient optical systems, e.g., fiber optics, waveguides, multilayer dielectric stacks (e.g., dielectric reflectors), etc., the approach provides an efficient use of illumination (e.g., laser) power. For example, illumination of a substrate comprising many separate reaction sites, "detection regions," or "observation regions" using waveguide arrays as described herein can reduce the illumination power ~10- to 1000-fold as compared to illumination of the same substrate using a free space illumination scheme comprising, for example, separate illumination (e.g., via laser beams) of each reaction site. In general, the higher the multiplex (i.e., the more surface regions to be illuminated on the substrate), the greater the potential energy savings offered by the waveguide illumination schemes provided herein. In addition, since waveguide illumination need not pass through a free space optical train prior to reaching the surface region to be illuminated, the illumination power can be further reduced.

In addition, because illumination is provided from within confined regions of the substrate itself (e.g., optical waveguides), issues of illumination of background or non-relevant regions, e.g., illumination of non-relevant materials in solutions, autofluorescence of substrates, and/or other materials, reflection of illumination radiation, etc., are substantially reduced.

In addition to mitigating autofluorescence of substrate materials, the systems described herein substantially mitigate autofluorescence associated with the optical train. In particular, in typical fluorescence spectroscopy, excitation light is directed at a reaction of interest through at least a portion of the same optical train used to collect signal fluorescence, e.g., the objective and other optical train components. As such, autofluorescence of such components will contribute to the detected fluorescence level and can provide signal noise in the overall detection. Because the systems provided herein direct excitation light into the substrate through a different path, e.g., through an optical fiber optically coupled to the waveguide in the substrate, this source of autofluorescence is eliminated.

Waveguide-mediated illumination is also advantageous with respect to alignment of illumination light with surface regions to be illuminated. In particular, substrate-based analytical systems, and particularly those that rely upon fluorescent or fluorogenic signals for the monitoring of reactions, typically employ illumination schemes whereby each analyte region must be illuminated by optical energy of an appropriate wavelength, e.g., excitation illumination. While bathing or flooding the substrate with excitation illumination serves to illuminate large numbers of discrete regions, such illumination may suffer from the myriad complications described above. To address those issues, targeted excitation illumination may serve to selectively direct separate beams of excitation illumination to individual reaction regions or groups of reaction regions, e.g. using waveguide arrays. When a plurality, e.g., hundreds or thousands, of analyte regions are disposed upon a substrate, alignment of a separate illumination beam with each analyte region becomes technically more challenging and the risk of misalignment of the beams and analyte regions increases. Alignment of the illumination sources and analyte regions may be built into the system, however, by integration of the illumination pattern and reaction regions into the same component of the system, e.g., a waveguide substrate. In some cases, optical waveguides may be fabricated into a substrate at defined regions of the substrate, and analyte regions are disposed upon the area(s) of the substrate occupied by the waveguides.

Finally, substrates used in the waveguides may be provided from rugged materials, e.g., silicon, glass, quartz or polymeric or inorganic materials that have demonstrated longevity in harsh environments, e.g., extremes of cold, heat, chemical compositions, e.g., high salt, acidic or basic environments, vacuum and zero gravity. As such, they provide rugged capabilities for a wide range of applications.

Waveguide substrates used in the devices and methods of the present invention generally include a matrix, e.g., a silica-based matrix, such as silicon, glass, quartz or the like, polymeric matrix, ceramic matrix, or other solid organic or inorganic material conventionally employed in the fabrication of waveguide substrates, and one or more waveguides disposed upon or within the matrix, where the waveguides are configured to be optically coupled to an optical energy source, e.g., a laser. Such waveguides may be in various conformations, including but not limited to planar waveguides and channel waveguides. Some preferred embodiments of the waveguides comprise an array of two or more waveguides, e.g., discrete channel waveguides, and such waveguides are also referred to herein as waveguide arrays. Further, channel waveguides can have different cross-sectional dimensions and shapes, e.g., rectangular, circular, oval, lobed, and the like; and in certain embodiments, different conformations of waveguides, e.g., channel and/or planar, can be present in a single waveguide substrate.

In typical embodiments, a waveguide comprises an optical core and a waveguide cladding adjacent to the optical core, where the optical core has a refractive index sufficiently higher than the refractive index of the waveguide cladding to promote containment and propagation of optical energy through the core. In general, the waveguide cladding refers to a portion of the substrate that is adjacent to and partially, substantially, or completely surrounds the optical core. The waveguide cladding layer can extend throughout the matrix, or the matrix may comprise further "non-cladding" layers. A "substrate-enclosed" waveguide or region thereof is entirely surrounded by a non-cladding layer of matrix; a "surface-exposed" waveguide or region thereof has at least a portion of the waveguide cladding exposed on a surface of the substrate; and a "core-exposed" waveguide or region thereof has at least a portion of the core exposed on a surface of the substrate. Further, a waveguide array can comprise discrete waveguides in various conformations, including but not limited to, parallel, perpendicular, convergent, divergent, entirely separate, branched, end-joined, serpentine, and combinations thereof.

A surface or surface region of a waveguide substrate is generally a portion of the substrate in contact with the space surrounding the substrate, and such space may be fluid-filled, e.g., an analytical reaction mixture containing various reaction components. In certain preferred embodiments, substrate surfaces are provided in apertures that descend into the substrate, and optionally into the waveguide cladding and/or the optical core. In certain preferred embodiments, such apertures are very small, e.g., having dimensions on the micrometer or nanometer scale, as described further below.

It is an object of devices and methods of the invention to illuminate analytes (e.g., reaction components) of interest and to detect signal emitted from such analytes, e.g., by excitation and emission from a fluorescent label on the analyte. Of particular interest is the ability to monitor single analytical reactions in real time during the course of the reaction, e.g., a single enzyme or enzyme complex catalyzing a reaction of interest. The waveguides described herein provide illumination via an evanescent field produced by the escape of optical energy from the optical core. The evanescent field is the optical energy field that decays exponentially as a function of distance from the waveguide surface when optical energy passes through the waveguide. As such, in order for an analyte of interest to be illuminated by the waveguide, it must be disposed near enough to the optical core to be exposed to the evanescent field. In preferred embodiments, such analytes are immobilized, directly or indirectly, on a surface of the waveguide substrate. For example, immobilization can take place on a surface-exposed waveguide, or within an aperture in the substrate. In some preferred aspects, analyte regions are disposed in apertures that extend through the substrate to bring the analyte regions closer to the optical core. Such apertures may extend through a waveguide cladding surrounding the optical core, or may extend into the core of the waveguide.

In certain embodiments, such apertures also extend through a mask layer above the surface of the substrate. In preferred embodiments, such apertures are "nanoholes," which are nanometer-scale holes or wells that provide structural confinement of analytic materials of interest within a nanometer-scale diameter, e.g., ~10-100 nm. In some embodiments, such apertures comprise optical confinement characteristics, such as zero-mode waveguides, which are also nanometer-scale apertures and are further described elsewhere herein. Although primarily described herein in terms of channel waveguides, such apertures could also be constructed on a planar waveguide substrate, e.g., where the planar waveguide portion/layer is buried within the substrate, i.e., is not surface-exposed. Regions on the surface of a waveguide substrate that are used for illumination of analytes are generally termed "analyte regions", "reaction regions", or "reaction sites", and are preferably located on a surface of the substrate near enough to an optical core to be illuminated by an evanescent wave emanating from the optical core, e.g., on a surface-exposed waveguide or at the bottom of an aperture that extends into the substrate, e.g., into the waveguide cladding or core. The three-dimensional area at a reaction site that is illuminated by the evanescent field of a waveguide core (e.g., to an extent capable of allowing detection of an analyte of interest) is generally termed the "observation volume" or "illumination volume". A region of a waveguide substrate that comprises one or more analyte regions is generally referred to as a "detection region" of the substrate, and a single substrate may have one or multiple detection regions. Examples of such optical waveguides are provided in in U.S. Pat. No. 7,820,983 and U.S. Patent Application Publication No. 2012/0085894, as described above.

The present invention provides devices for waveguide-based illumination of analyte regions in apertures (e.g., nanoholes or ZMWs) that in some cases reduce the variation in illumination, for example, by mitigating propagation losses over the length of the waveguide. Such propagation losses can be further exacerbated by a metal layer disposed over the surface of the substrate, because it can absorb optical energy from a surface-exposed or core-exposed waveguide, or even a waveguide near to the surface of the substrate. Such metal layers are typically found in conventional ZMW arrays, presenting a challenge for combining such arrays with waveguide illumination strategies.

One of the limitations of waveguide illumination is optical attenuation as the light propagates down the guide resulting in a reduction in power at different locations in the guide. For example, a particular laser intensity coupled into the waveguide will experience a slow decrease in energy density as light travels down the guide due to propagation losses, with the highest power at the end nearest the illumination source and the lowest at the end farthest from the illumination source. The degree of the propagation loss is typically a function of the designed geometry and manufacturing tolerances, and presents a challenge to performing multiplexed analytical reactions because it constrains the spatial range of the usable waveguide structure. It is important to maximize the distance over which the laser intensity is sufficiently uniform, in order to maximize the multiplex capabilities of the system. It is therefore an object of the present invention to provide uniform power over the length of a waveguide, e.g., to promote uniform illumination of all reaction sites to be illuminated by the waveguide.

In certain embodiments, a waveguide is tapered such that the core gradually becomes thinner along the direction of propagation. This causes the degree of light confinement to be gradually increased, which can offset the gradual reduction in the total amount of power in the guide due to propagation losses and essentially maintain a desired mode shape and field strength for the optical energy propagated over the length of the waveguide core. In principle, the sum of propagation losses is balanced by the decreasing core size such that uniformity of evanescent field strength can be held constant for an arbitrarily long distance, with limitations to the strength of the evanescent field also being dependent on the starting laser power and the starting waveguide core dimensions. For a given waveguide substrate, once the propagation loss is determined the waveguide geometry can be designed to smoothly vary, thereby modifying the degree of confinement such that the relative field strength at the point of interest increases at the same rate that propagation losses reduce the total power in the guide. For example, a tapered waveguide core can be widest at the portion most proximal to the light source, slowly narrowing along the guide, with the field localization increasing at the same rate that propagation losses are reducing the waveguide field strength. The tapering can take place in any direction including the z direction (top to bottom), the y direction (side to side), or a combination thereof.

In certain embodiments, a waveguide cladding above a waveguide core in a waveguide substrate is tapered such that the waveguide core is slowly brought closer to the reaction sites at the surface of the substrate by an ever-decreasing width of the waveguide cladding layer that separates the core from the reaction sites. As such, although there is propagation loss from the waveguide, as the field strength in the waveguide decreases, it is brought closer to the reaction sites, and this increasing proximity compensates for an overall reduced field strength. In some embodiments, both the waveguide cladding layer and waveguide core are tapered to mitigate loss of field strength due to propagation losses.

Local Field Enhancement

In certain embodiments, the waveguides used in some of the devices disclosed herein comprise a specific feature associated with each aperture, a local field enhancement element, to increase the efficiency of sample illumination. Such a feature serves to improve the coupling efficiency between the waveguide and the illumination volume, particularly when the apertures are subwavelength apertures in a metal layer disposed over the surface of the substrate. For example, in some embodiments, the local field enhancement element is a layer of a material in the vicinity of each aperture that has a higher dielectric constant than the cladding layer or that is a metal, such as, for example, copper, silver, gold, or aluminum. One example of this type of local field enhancement element is shown in FIG. 7A, where the local field enhancement element corresponds to a ring or other geometric pattern of high dielectric material or metal 706 surrounding the aperture 702, just below the opaque, metal layer 704. As shown in FIG. 7A, a pattern of high dielectric material, such as $Al_2O_3$, or a metal, couples energy from the waveguide core of high dielectric 708, such as $Si_3N_4$, through the cladding of low dielectric 710, such as $SiO_2$. Other suitable materials of high dielectric material may be substituted for $Al_2O_3$, as would be understood by those of ordinary skill in the art.

The material of high dielectric or metal surrounding the aperture may serve other purposes in addition to improving the coupling of excitation light to the illuminated volume within the aperture. For example, if this material is deposited such that it is exposed to the solution to be analyzed, it may act as a distinct surface for immobilization of biomaterials or to prevent immobilization of those materials. Specifically, there may be advantages in providing different surfaces on the bottom and sides of the aperture to allow, for example, for biased immobilization of reaction components. See, e.g., U.S. Patent Publication No. 2012/0085894. For example, as shown in FIG. 7A, the sides of the nanowell/aperture may expose a material such as, e.g., the high dielectric material or the metal, whereas the bottom of the nanowell/aperture may expose the cladding material, e.g., glass. Selective deposition of analytes is preferably effected when there are chemical differences between the surfaces, as would be understood by those of ordinary skill in the art.

The local field enhancement element may include additional features to further enhance the efficiency of sample illumination by excitation light, to further decrease propagation losses of excitation light, or to provide other functions, such as, for example, enhancing the detection of light emitted from the sample. One such additional feature is exemplified in FIG. 7B, where a pattern of high dielectric material or metal 726 surrounds the nanowell/aperture 722 below the opaque, metal layer, 724. These patterns, for example a pattern of concentric rings surrounding the aperture, as shown in FIG. 7B, may act as a broad area coupler for the excitation light into the sample volume. They may additionally act to collimate light emitted from sample in the illuminated volume within the aperture, thus improving the detectability of that light. In this particular embodiment, the local enhancement element thus serves to couple light both into and out of the aperture. Also shown in FIG. 7B is the waveguide core of high dielectric 728, such as $Si_3N_4$, set within the cladding of low dielectric 730, such as $SiO_2$.

Aperture shapes, and the shape of the high dielectric material or metal surrounding the apertures, may additionally enhance the coupling of light energy from the waveguide core to the illuminated volume. See, for example, Sahin et al. (2011) *J. Nanophoton.* 5(1), 051812; doi: 10.1117/1.3599873. Subwavelength aperture shapes, including C-shaped apertures, triangle pairs, or diamond-shaped aperture structures may accordingly be usefully employed as local field enhancement elements according to this aspect of the invention.

Figure 7C:
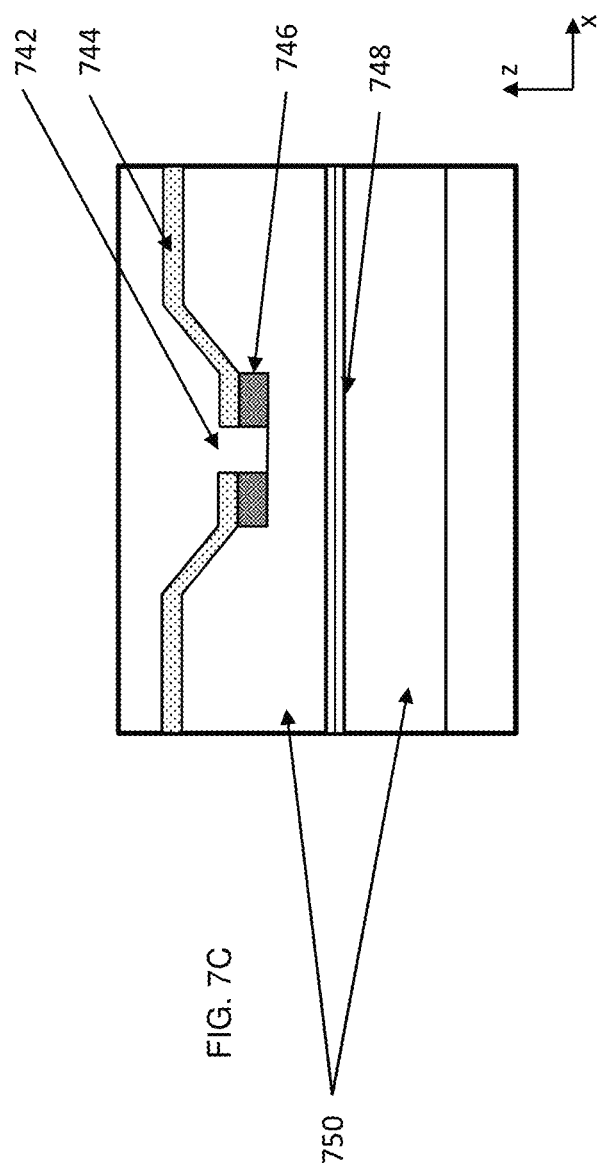
FIG. 7C illustrates another alternative device structure, having a decreased cladding thickness in the regions of the waveguide adjacent to the aperture and/or an increased cladding thickness in the regions not adjacent to the aperture. The device of FIG. 7C additionally includes a high dielectric material or metal in the vicinity of the aperture.

In yet another embodiment, the local field enhancement element corresponds to increasing the thickness of the cladding in the regions of the waveguide that are not adjacent to the aperture and/or decreasing the thickness of the cladding in the regions of the waveguide that are adjacent to the aperture. This embodiment provides, for example, for decreased propagation losses, due to the increased distance between the light beam and the metallic layer, and for increased coupling efficiency, due to the positioning of the aperture closer to the evanescent wave. As shown in FIG. 7C, decreasing the thickness of the cladding 750 (e.g., $SiO_2$) in the region around the aperture 742 by recessing the aperture improves the coupling of light energy into the illumination volume. Increasing the thickness of the cladding in regions remote from the aperture decreases propagation losses resulting from interactions of the evanescent wave with the opaque metallic layer 744. FIG. 7C also shows an additional optional local field enhancement element in the form of a ring of high dielectric material or metal 746 surrounding the aperture below the opaque metallic layer. As noted above, this element can be a ring or other pattern of high dielectric material or metal in the vicinity of the aperture, just below the opaque metallic layer. Combinations of different local field enhancement elements may thus provide synergistic improvements in the coupling of light energy from the waveguide core to the illuminated volume and are considered within the scope of the invention. Also shown in FIG. 7C is the waveguide core of high dielectric 748, such as $Si_3N_4$, set within the cladding of low dielectric 750.

FIGS. 8A and 8B illustrate top-down and cross-sectional views of another embodiment of the analytical device, similar to the device of FIG. 7C, in which the aperture is surrounded by a ring of high dielectric or metal 806 and is recessed to bring it closer to the waveguide core. (Note that the opaque, metallic layer 804 is omitted from the top-down view shown in FIG. 8A.) This embodiment also includes an additional optional feature of this aspect of the invention, a stray-light termination element 812. Such a design feature can decrease background signal by blocking scattered light from the excitation source and potentially also autofluorescence from materials within the device. The material used in the stray-light termination element is selected from materials that selectively absorb light to be blocked from reaching the detector layer of the device, as would be understood by one of ordinary skill in the art. Also shown in FIGS. 8A and 8B is the waveguide core of high dielectric 808, such as $Si_3N_4$, set within the cladding of low dielectric 810, such as $SiO_2$. Exemplary dimensions for the device are indicated in FIG.

Figure 9C:
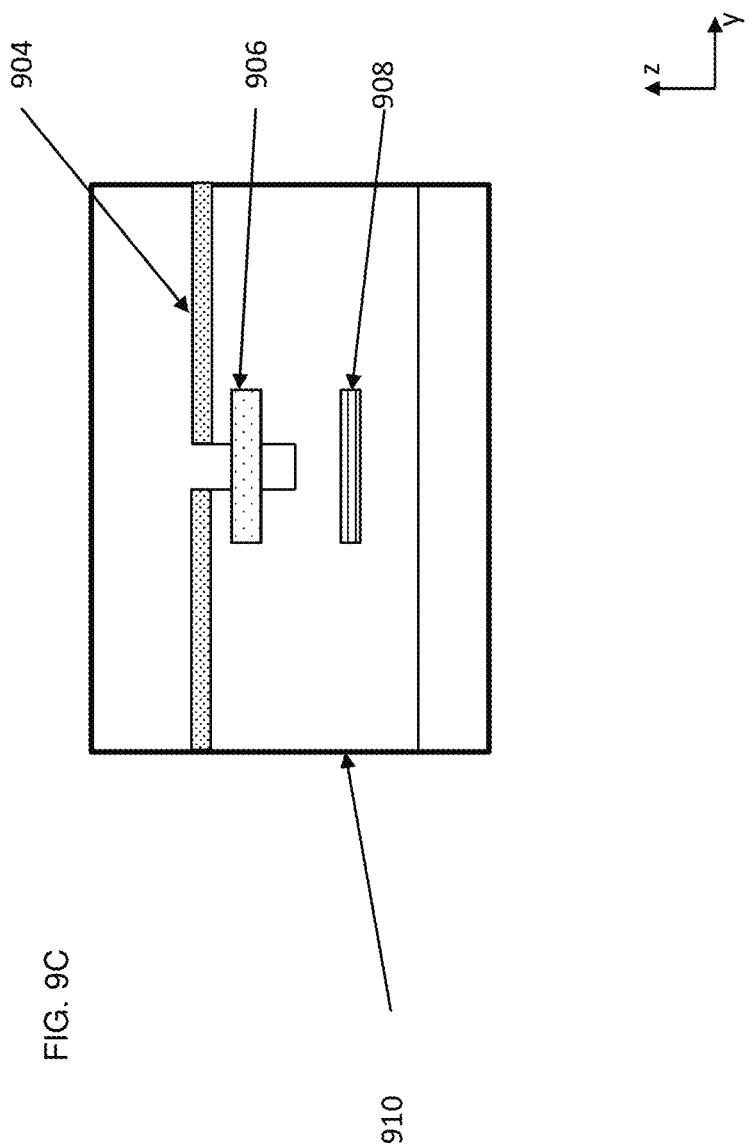

FIGS. 9A-9C illustrate a device configuration used in a mathematical simulation of the effectiveness of the above designs, specifically increasing the cladding thickness in regions not adjacent to the aperture and including a ring of metal 906 in the vicinity of the aperture. (Note that the opaque, metallic layer 904 is omitted from the top-down view shown in FIG. 9A.) In particular, the simulations involve a finite-difference time-domain (FDTD) solution of the Maxwell equations. See Taflove and Hagness (2004) *Computational Electrodynamics: The Finite-Difference Time-Domain Method, Third Edition*. FIGS. 9A-9C also show the waveguide core of high dielectric 908, such as Si$_3$N$_4$, set within the cladding of low dielectric 910, such as SiO$_2$.

The simulations using the device configuration of FIGS. 9A-9C demonstrate that by increasing the cladding thickness between ZMWs by 200 nm, the propagation loss, for example, due to proximity to the metallic layer, decreases from over 100 dB/mm to ~14 dB/mm, allowing a lower laser power to illuminate several ZMWs. Overall illumination efficiency of the fluorophore is kept high, so as to keep the total laser power in the waveguide low, thus helping to limit autofluorescence generated in the waveguide. In addition, a metal ring (or cylindrical shell) in the vicinity of the aperture provides enough metal to enhance the coupling to the ZMW but not so much as to create waveguide loss. While any metal could be used, metals such as copper, silver, gold, and aluminum are preferred. Typical metal thicknesses (i.e., shell thickness) around the aperture are 100-400 nm. Since aperture diameters are preferably in the range of 100-200 nm, and most preferably approximately 140 nm, the outer diameter of the metal ring is therefore preferably from 340 nm to 1 μm, although outer ring diameters of from about 0.2 to 2 μm, or even higher, are contemplated.

Dimensional Modulation of Waveguides

Figure 10A:
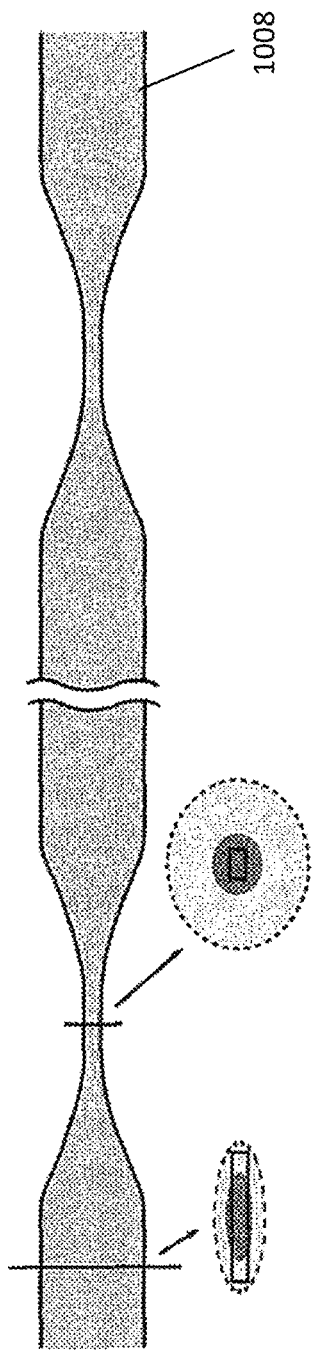
FIGS. 10A and 10B illustrate an example of the dimensional modulation of the waveguides.
Figure 10B:
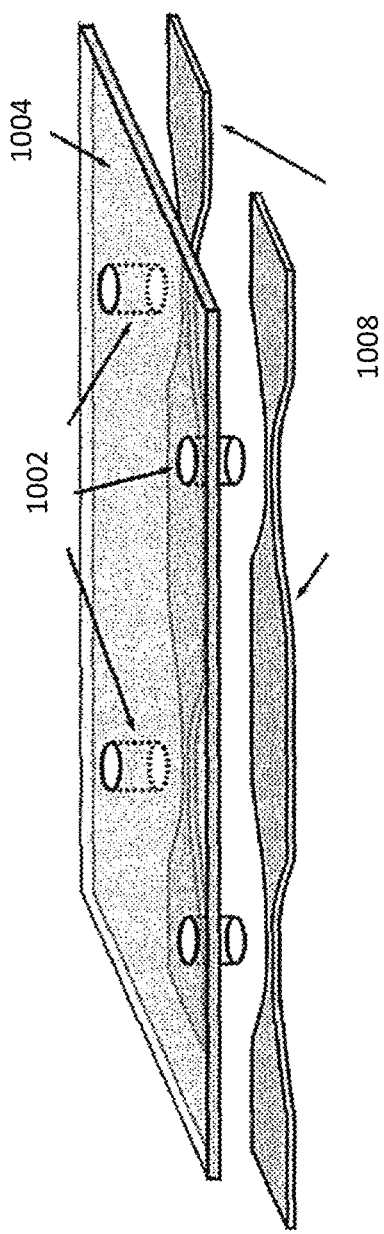

As noted above, efficient coupling of excitation light into the illumination volume requires that the optical waveguide be sufficiently close to the nanometer-scaled apertures, but placement of the optical waveguide too close to the metallic layer in which the apertures are disposed may cause propagation losses. In order to overcome these limitations, in another aspect of the invention, the optical waveguide is placed sufficiently far from the metallic layer to avoid propagation losses, and the cross-sectional area of the waveguide is modulated in the vicinity of the apertures to enlarge the mode size and thus increase the coupling of light into the illuminated volume. In general, waveguide core dimensions are designed to satisfy the single-mode condition, as well as confining the mode compactly around the core region. In preferred embodiments, the cross-sectional area of the optical core is decreased at locations where the optical waveguide illuminates the apertures. In some embodiments, the decrease in cross-sectional area of the optical core is achieved using adiabatic tapers in order to avoid extra power loss. In preferred embodiments, and as illustrated in FIGS. 10A and 10B, the thickness of the optical waveguide is kept constant, while the cross-sectional area of the optical core is modulated by varying the width of the optical core. Specifically, FIG. 10A provides a top-down view of waveguide 1008 with cross-sectional views of a normal section of the waveguide with compact mode size (left cross-section) and a tapered-down section of the waveguide with expanded mode size (right cross-section). FIG. 10B provides a three-dimensional perspective of the exemplary device showing locations of nanowell/apertures 1002 within the opaque, metal layer 1004 covering the array. Also shown are dimension-modulated waveguides 1008 positioned below the nanowell/apertures. Fabrication of the core layer in this embodiment is simplified, because the core thickness is uniform. In some embodiments, the optical signal passing through the waveguide core is transverse electric (TE) polarized light. These embodiments provide advantages when the cross-sectional area of the waveguide is modulated by varying the width of the waveguide core, because the mode size of TE-polarized light is most strongly affected by the waveguide width.

In variants of the just-described aspect of the invention, the width of the optical waveguide is kept constant, while the cross-sectional area of the optical core, and thus the mode size of the transmitted light, is modulated by varying the thickness of the optical core. As above, the cross-sectional area of the optical core is decreased at locations where the optical waveguide illuminates the apertures in order to maximize coupling to the illuminated volume. In some embodiments, the optical signal passing through the waveguide core is transverse magnetic (TM) polarized light, since the mode size of TM-polarized light is most strongly affected by the waveguide thickness, as would be understood by one of ordinary skill in the art.

In some embodiments of the invention, dimensional modulation of the waveguides and local field enhancements may be usefully combined. For example, modulation of the cross-sectional area of the optical core at each aperture may be usefully combined with a pattern of high dielectric material or metal in the vicinity of each aperture, for example, below the metallic layer. Such combinations provide yet further improvement in the efficiency of coupling of optical energy from the waveguide to the illuminated volume.

By way of non-limiting example, the typical waveguide widths for use in the analytical devices of the instant invention range from 100 nm to 1000 nm. Such widths therefore correspond to roughly 0.3 to 3.0 wavelengths in a situation where the wavelength of excitation light propagated along the waveguide is 335 nm. (It should be noted that the wavelength of photons in a waveguide may be significantly shifted from that of the same photons traveling through air.) In some embodiments of the invention, the width of the waveguide optical core is decreased by 5 to 90% at locations where the evanescent field illuminates the nanometer-scale apertures, compared to locations where the evanescent field does not illuminate the apertures (in other words, the optical core is decreased from 0.15 wavelengths to 2.7 wavelengths for a core that is 3.0 wavelengths wide). In some embodiments, the width of the waveguide optical core is decreased by 5 to 50% at locations where the evanescent field illuminates the apertures, compared to locations where the evanescent field does not illuminate the apertures (i.e., from 0.15 wavelengths to 1.5 wavelengths in a 3.0 wavelength wide core). In preferred embodiments, the width of the waveguide optical core is decreased by 10 to 20% at those locations (i.e., from 0.30 wavelengths to 0.60 wavelengths). As noted above, it is desirable in the devices of this aspect of the invention for the changes in width/cross-sectional area to be gradual, preferably adiabatic, in order to avoid an additional mechanism for propagation losses. Such gradual tapering—narrower in the locations near the nanometer-scale apertures and wider in the locations away from the nanometer-scale apertures—can be readily be optimized in the design of the device, using analytical calculations, as would be understood by one of ordinary skill in the art.

Waveguide Core Positioning

In another aspect of the invention, the configuration and positioning of the waveguide core is varied in order to maximize collection of signal photons while suppressing collection of background photons (e.g., scattered light and autofluorescence). In particular, in these embodiments the waveguide core is positioned so that it is not directly between the nanometer-scaled apertures and their corresponding detectors. In preferred embodiments, the illuminated volume in each aperture is illuminated by evanescent fields emanating from two or more optical cores. In some embodiments, the device further contains an opaque layer disposed between the waveguide layer and the detector layer. The opaque layer contains a plurality of openings positioned to allow signal photons from the sample to pass unimpeded into the detector. The opaque layer would thus decrease access of photons from, for example, autofluorescence or scattering emanating from the waveguide cores, to the detector, and thus decrease background signal. As would be understood by one of ordinary skill in the art, signal photon collection is defined by photon flux through the opening in the opaque material, and collection efficiency is modulated by the dimensions of the opening and the optical distance from the signal source. Likewise, collection of autofluorescence and scattered light from the waveguide core through the opening is governed by the dimensions of the opening and the solid angle occupied by the waveguide as viewed from the opening.

By using a waveguide that is not positioned directly between the nanometer-scaled aperture and the detector, i.e., a "slot" waveguide, the waveguide core, and associated autofluorescence and scattering, is moved away from a direct path to the detector, thus increasing the angle of incidence into the detector and decreasing background signal. Furthermore, slot waveguides may provide increased optical fields in the regions of low refractive index between the high-index cores, and thus increase coupling of optical energy from the waveguides to the illuminated volume. See, for example, Feng et al. (2006) *IEEE J. Quantum Electron.* 42, 885; Sun et al. (2007) *Optics Express* 15, 17967. Optical sensing devices making use of slot waveguides have been described. See, for example, Barrios (2006) *IEEE Photon Technol. Lett.* 18, 2419; Barrios et al. (2007) *Optics Letters* 32, 3080; Barrios et al. (2008) *Optics Letters* 33, 708; Robinson et al. (2008) *Optics Express* 16, 4296. The signal-to-background ratio in devices of the instant invention that utilize a slot waveguide format may be optimized, for example, by varying the dimension of the openings in the opaque layer and by varying the configuration of the waveguide (e.g., spacing between separate optical cores and distance between waveguide core, opaque layer, and detector layer), as would be understood by those of ordinary skill in the art.

Figure 11A:
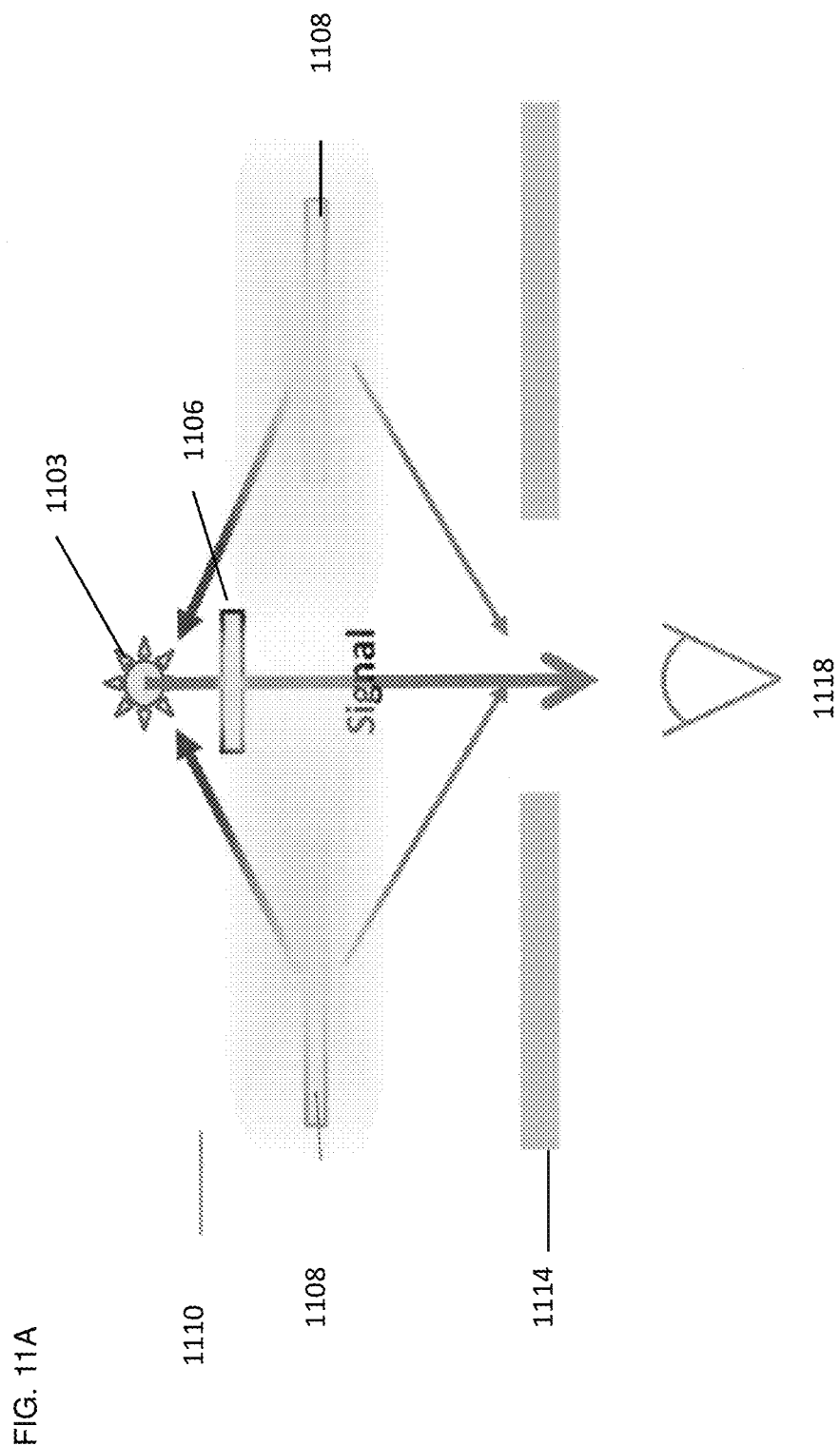
FIGS. 11A and 11B illustrate an example of a device with a "slotted" waveguide.
Figure 11B:
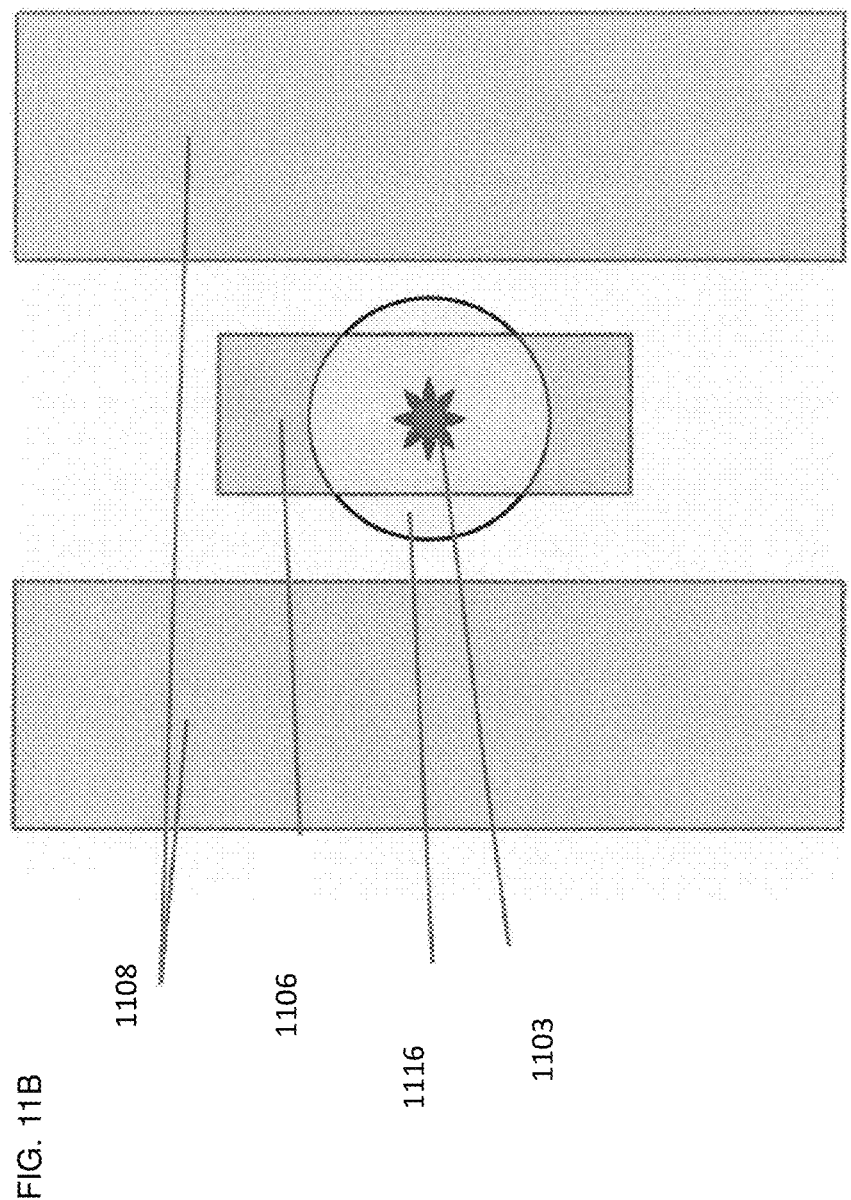

FIGS. 11A and 11B illustrate an example of this aspect of the invention that includes an optional local field enhancement element to increase further the coupling of excitation energy to the illuminated volume. In particular, FIG. 11A, illustrates a cross-sectional view of the device down the length of the divided (i.e., "slot") waveguide cores 1108, surrounded by cladding of low dielectric 1110. As shown, the evanescent waves emanating from the separate cores overlap and jointly illuminate the sample "signal source" 1103 within a nanowell/aperture at the top of the drawing. The local field enhancement element 1106 is illustrated in this drawing as a rectangle below the sample. This element could, for example, correspond to a material of high dielectric constant or metal patterned in the area adjacent to the nanometer-scale apertures, as described above. As also described more fully above, this element serves to increase coupling between the waveguide core and the sample within the nanometer-scale apertures and thus increase signal emission from the sample. Such increased coupling could further increase the signal-to-background ratio in the devices of the invention by decreasing the size of the field necessary in the core and thus decreasing the associated autofluoresence and scattering.

FIG. 11A further illustrates the opaque layer 1114, which is positioned between the waveguide layer and the detector 1118, and the opening in the opaque layer to allow emission signal from the illuminated volume to pass to the detector. The opaque layer is fabricated from any material suitable for attenuating transmission of excited light from the waveguide core to the detector, e.g., a metal layer of sufficient thickness. As shown in FIG. 11A, the positioning of the waveguide cores away from a direct alignment between the nanometer-scale aperture (not shown, but surrounding the illuminated sample volume) and the detector does not greatly diminish the efficiency of excitation of the illuminated volume, particularly if an optional local enhancement element is included to enhance the coupling, but causes a significant decrease in the transmission of autofluorescence or scattered light to the detector, due to the presence of the opaque layer.

FIG. 11B provides a top-down view of the analytical device shown in FIG. 11A, including the divided waveguide cores 1108. The "signal source" 1103, which corresponds to the illuminated volume of the sample, is above the plane of the drawing, and the opaque layer, including the "opening" 1116 in the opaque layer over the detector is below the plane of the drawing. The local enhancement element 1106 is illustrated as a rectangular block, but any of the local enhancement elements described above could usefully be included in the device to enhance coupling of excitation energy to the sample volume. The detector is not shown in this drawing but would be positioned below the opening and in line with the signal source.

Waveguide Frequency Conversion

As noted above, excitation light is typically provided to sample volumes via guided optics. Part of the motivation for this approach lies in the possibility of dispensing with the disadvantages of classic free-space optics by directing the sum total of excitation light needed to excite the illumination volumes in all of the nanometer-scale apertures through a single optical system and onto a single chip. The guided optical approach can involve some disadvantages of its own, however, including alignment complexity, cumulative autofluorescence, scattering, and cumulative laser heating. The latter three issues in particular are straightforward limitations that result from the material properties of the optical system. The traditional chemistry and chemical formulations used in fluorescence-based nucleic acid sequencing contribute to the difficulties, as photonic excitation must be delivered within a fairly narrow range of wavelengths, and the resulting emission wavelengths are only slightly longer. Consequently, autofluorescence of the system generally occurs within the same region of the spectrum as the desired fluorescence emission signals and can therefore be a significant limitation on the optical signal-to-noise ratio that can be achieved in a given system. Scattering can also be a detriment to signal-to-noise, because it is difficult to control the direction that scattered light travels as it leaves the guided mode, and some fraction may arrive at a sensor, adding noise. Such scattered light may be difficult to filter out based on its wavelength. Similarly, photonic heating caused by non-negligible absorption of the materials used to construct the optical system and the sample chip is a strong function of the excitation wavelength, and there is little flexibility in altering this parameter given the limitations in reagents used in typical sequencing reactions.

Accordingly, in another aspect of the invention, the limitations of a typical multiplexed sequencing system are addressed by using optical techniques such as harmonic generation, four-wave mixing, and stimulated raman scattering to manipulate the wavelengths of pump excitation away from those necessary for sample illumination and detection and toward spectral regions that are more suitable for the optical system, particularly with respect to the effects of the excitation photons on autofluorescence, laser heating, propagation loss, signal-to-background ratios, etc. Specifically, it is generally beneficial for excitation light to be transported as longer-wavelength photons, for example as infrared photons, which generate less autofluorescence within the device and which result in less laser heating. Shorter-wavelength light can be generated at predetermined locations, as desired, preferably only in the locations necessary to excite the relevant samples. Waveguide frequency conversion can be effected by only slight modifications in optical parameters through phase matching, or it can be actively switched on and off through electro-optical effects that modify the refractive index of one or more materials. Thus, light can be transported as an infrared pump and then be efficiently coupled into shorter wavelength harmonic waveguide modes as desired. An additional advantage of such delivery of waveguide light is that scattering of light is dramatically reduced, because the infrared pump wavelength is significantly different in wavelength from the signal being collected by the detector, thereby reducing the detrimental impact of scattering on the signal-to-noise ratio.

Wavelength conversion in waveguides is typically effected through second harmonic generation (SHG), wherein efficient conversion involves three features: a nonlinear optical (NLO) material (in the case of SHG, for example, a noncentrosymmetric material that responds to electromagnetic fields with higher polarization multipoles), phase matching (typically with equal group velocities on both propagating modes), and sufficient overlap integral (for example, where the energy density overlaps between the fundamental mode, the harmonic mode, and the nonlinear material in the structure). All three features can be designed into a waveguide structure, and all three can be selected or adjusted by a variety of techniques that are well understood by those of ordinary skill in the art. Furthermore, the techniques are widely available and are already being used in numerous commercial applications. In addition to SHG, similar techniques have been applied to other nonlinear optical interactions including optical parametric amplification (OPA) and stimulated Raman scattering. Such alternative approaches should also be considered within the scope of the instant invention.

At a fundamental level, periodic poling may be used to determine where light is converted from longer wavelengths, for example infrared wavelengths, to wavelengths usefully utilized in the direct excitation of samples, for example visible wavelengths. Such periodic poling may be divided generally into two branches, a fixed periodic poling, which would not change in time, and a dynamic periodic poling, which can be used to fine-tune the wavelength conversion and to switch on or off the conversion at any location or set of locations, and at any time. The programmability of such approaches is of particular value in the application of periodic poling to wavelength conversion for use in the sequencing methods described herein. Application of these techniques, including, for example, materials used, methods of fabrication, optical properties, theoretical principles, methods of tuning, conversion efficiencies, and so forth, are known in the art. See, for example, Yao and Wang, *Quasi-Phase-Matching Technology*, in *Nonlinear Optics and Solid-State Lasers*, Springer Series in Optical Sciences 164, Springer-Verlag Berlin Heidelberg 2012. Specific examples of the use of fixed and dynamic periodic poling in wavelength conversion devices have also been reported. See Laurell et al. (2012) *Optics Express* 20, 22308; Chen et al. (2012) *Optics Letters* 37, 2814; Nava et al. (2010) *Electronics Letters* 46, 1686; Pan et al. (2010) *Optics Communications* 284, 429.

Figure 12A:
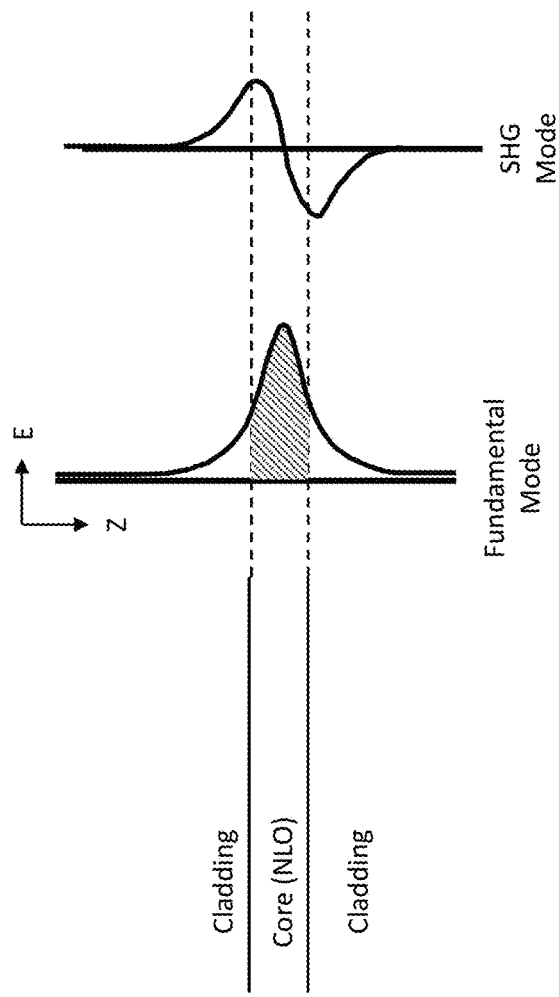
FIGS. 12A and 12B show the configuration and optical modes of a waveguide containing a non-linear optical material in the core (FIG. 12A) and in part of the cladding (FIG. 12B).
Figure 12B:
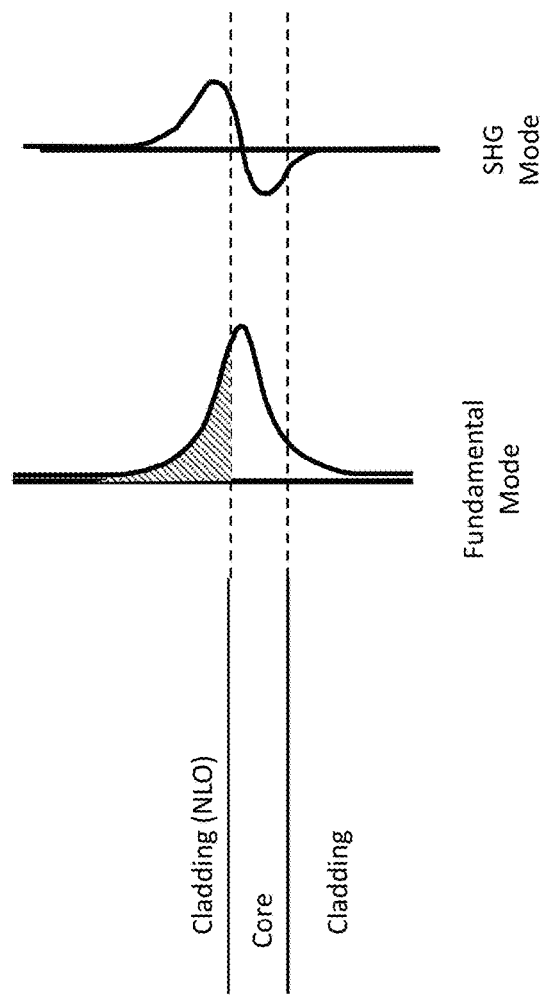

An example of a basic SHG waveguide usefully employed in the devices of the instant invention is illustrated in FIG. 12A, where the nonlinear medium is present in the core material of the waveguide, thus simplifying the overlap integral. An alternative structure, wherein the nonlinear medium is present in part of the cladding material, is shown in FIG. 12B.

Figure 13A:
FIGS. 13A and 13B illustrate configurations of waveguides containing non-linear optical materials.
Figure 13B:
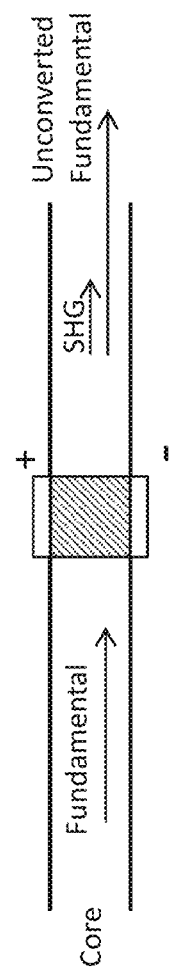

FIG. 13A illustrates phase matching by periodic NLO materials. Such an approach can allow significantly relaxed fabrication tolerances compared to situations where phase matching is not provided by such periodicity. FIG. 13B illustrates phase modulation by electro-optic effects. It should be noted in this context that virtually all SHG materials also exhibit the strong Pockels coefficients that are important for this electro-optical effect.

The approaches for waveguide frequency conversion described herein can be incorporated into the architecture of an analytical device in a variety of ways. For example, as shown in FIG. 14A, SHG conversion may take place just after light is coupled into the chip. Alternatively, or in addition, excitation light may be injected into the waveguide and converted into SHG at predetermined locations, as shown in FIG. 14B. In some embodiments, excitation light can be programmed such that different regions of nanometer-scale apertures and their corresponding illuminated volumes can be switched on and off independently.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. An analytical device comprising:
    a surface of the analytical device;
    an array of apertures; and
    an optical waveguide comprising an optical core and a cladding;
    wherein the array of apertures is an array of nanometer-scale wells disposed in a metallic layer on the surface of the analytical device above the optical waveguide, such that optical energy passing through the optical core of the optical waveguide illuminates at least one nanometer-scale well in the array of nanometer-scale wells;
    wherein the metallic layer surrounding the at least one nanometer-scale well is recessed from the surface of the analytical device.

2. The analytical device of claim 1, further comprising a plurality of local field enhancement elements associated with the array of nanometer-scale wells.

3. The analytical device of claim 2, wherein the plurality of local field enhancement elements comprise a high dielectric material or metal, wherein the high dielectric material has a higher dielectric constant than silicon dioxide.

4. The analytical device of claim 3, wherein the high dielectric material or metal is arranged in a geometric pattern around the nanometer-scale wells.

5. The analytical device of claim 4, wherein the geometric pattern is selected from the group consisting of a circle, a series of concentric circles, a C aperture, a triangle pair, and a diamond.

6. The analytical device of claim 3, wherein the high dielectric material or metal is $Al_2O_3$, copper, silver, gold, or aluminum.

7. The analytical device of claim 6, wherein the high dielectric material or metal is $Al_2O_3$.

8. The analytical device of claim 6, wherein the high dielectric material or metal is copper.

9. The analytical device of claim 1, wherein the optical core and the metallic layer are separated by a first thickness that is decreased at a location where an evanescent field emanating from the optical waveguide illuminates the at least one nanometer-scale well.

10. The analytical device of claim 9, wherein the optical core and the metallic layer are separated by a second thickness of from 150 to 300 nm at a location where the evanescent field does not illuminate the at least one nanometer-scale well.

11. The analytical device of claim 10, wherein the second thickness is about 200 nm.

12. The analytical device of claim 1, wherein an evanescent field emanating from the optical waveguide illuminates a sample within the at least one nanometer-scale well.

13. The analytical device of claim 12, wherein the sample is a biological sample.

14. The analytical device of claim 13, wherein the biological sample comprises at least one nucleic acid.

15. The analytical device of claim 1, wherein the analytical device comprises at least 1,000, at least 10,000, at least 100,000, at least 1,000,000, or at least 10,000,000 nanometer-scale wells.

16. The analytical device of claim 1, further comprising a stray-light termination element disposed below the metallic layer.

* * * * *